(12) United States Patent
Zheng et al.

US010729792B2

(10) Patent No.: US 10,729,792 B2
(45) Date of Patent: Aug. 4, 2020

(54) TEXAPHYRIN-PHOSPHOLIPID CONJUGATES AND METHODS OF PREPARING SAME

(71) Applicant: UNIVERSITY HEALTH NETWORK, Toronto (CA)

(72) Inventors: Gang Zheng, Toronto (CA); Joseph Keca, Fonthill (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 2 days.

(21) Appl. No.: 15/567,294

(22) PCT Filed: Apr. 14, 2016

(86) PCT No.: PCT/CA2016/000114
§ 371 (c)(1),
(2) Date: Oct. 17, 2017

(87) PCT Pub. No.: WO2016/165006
PCT Pub. Date: Oct. 20, 2016

(65) Prior Publication Data
US 2018/0104364 A1 Apr. 19, 2018

Related U.S. Application Data

(60) Provisional application No. 62/148,839, filed on Apr. 17, 2015.

(51) Int. Cl.
*C07D 487/22* (2006.01)
*A61K 49/22* (2006.01)
*C07F 9/6561* (2006.01)
*C07F 9/10* (2006.01)
*C12P 17/18* (2006.01)

(52) U.S. Cl.
CPC .......... *A61K 49/227* (2013.01); *C07D 487/22* (2013.01); *C07F 9/106* (2013.01); *C07F 9/6561* (2013.01); *C12P 17/182* (2013.01)

(58) Field of Classification Search
None
See application file for complete search history.

(56) References Cited

U.S. PATENT DOCUMENTS 6,375,930 B2  4/2002  Young et al.

FOREIGN PATENT DOCUMENTS

| CA | 2182960 | 8/1995 |
|---|---|---|
| CN | 106659684 | 5/1917 |
| CN | 1225591 | 8/1999 |
| CN | 102573914 | 7/2012 |
| CN | 103857384 | 6/2014 |
| CN | 103930137 | 7/2014 |
| CN | 104080929 | 10/2014 |
| JP | 2000-512279 | 9/2000 |
| JP | 2013-507399 | 3/2013 |
| JP | 2014-532062 | 12/2014 |
| JP | 2015-506671 | 3/2015 |
| WO | WO 1995/29702 | 11/1995 |
| WO | WO 97/46262 | 12/1997 |
| WO | WO 2011/044671 | 4/2011 |
| WO | WO 2012/167350 | 12/2012 |
| WO | WO 2013/046163 | 4/2013 |
| WO | WO 2013/053042 | 4/2013 |
| WO | WO 2013/082702 | 6/2013 |
| WO | WO 2013/159185 | 10/2013 |
| WO | WO 2015/192215 | 12/2015 |

OTHER PUBLICATIONS

International Search Report and Written Opinion issued in International Application No. PCT/CA2016/000114 dated Jul. 8, 2016.
Magda et al., "Synthesis of Texaphyrin Conjugates", *Pure Appl. Chem.*, (2004), 76(2): 365-374.
Mody et al., "Texaphyrins: A New Approach to Drug Development", *Journal of Porphyrins and Phetalocyanines*, (2001), 5(2): 134-142.
Preihs et al., "Recent Developments in Texaphyrin Chemistry and Drug Discovery", *Inorganic Chemistry*, (2013), 52: 12184-12192.
Extended European Search Report Issued in Corresponding European Application No. 16779355.3, dated Sep. 6, 2018.
Lovell, et al., "Phorphysome Nanovesicles Generated by Porphyrin Bilayers for Use as Multimodal Biophotonic Contrast Agents," *Nature Materials*, 10(4); 1-21, 2011.
Sessler, et al., "Texaphyrins: Sythesis and Applications," *Accounts of Chemical Research*, 27(2); 43-50, 1994.
First Chinese Office Action and Search Report Issued in Chinese Application No. 201680035422X, dated Mar. 6, 2019.
Office Action Issued in Corresponding Chinese Patent Application No. 201680035422.X, dated Nov. 14, 2019.
Office Action Issued in Corresponding Japanese Patent Application No. 2017-554284, dated Jan. 8, 2020.

*Primary Examiner* — Jessica Worsham
(74) *Attorney, Agent, or Firm* — Norton Rose Fulbright US LLP

(57) ABSTRACT

There is provided herein, a texaphyrin-phospholipid conjugate, wherein the texaphyrin-phospholipid conjugate comprises a texaphyrin, texaphyrin derivative or texaphyrin analog covalently attached to a lipid side chain of a phospholipid.

20 Claims, 28 Drawing Sheets

Texaphyrin-Lipid Conjugate:

Gadolinium(III) Complex:

Free-Base Nanotexaphyrin:

Key: 1) texaphyrin-lipid, Mn(OAc)₂ in methanol; 2) Mn-texaphyrin-lipid; 3) lipid film; 4) Mn-nanotexaphyrin; A) NEt₃ at 0°C; B) DSPE-2KPEG, cholestrol, and evaporate; C) hydrated with PBS, and self-assemble.

Manganese (II) Complex:

A

Sunfire

B

Yttrium (III) Complex:

A

B

Cadmium (III) Complex:

Indium (III) Complex:

A

B

Bismuth (III) Complex:

Samarium (III) Complex:

A

B

Terbium (III) Complex:

A

B

Dysprosium (III) Complex:

A

B

Holmium (III) Complex:

A

B

Erbium (III) Complex:

Thulium (III) Complex:

A

B

Ytterbium (III) Complex:

Rhenium (II) Complex:

A

B

TEXAPHYRIN-PHOSPHOLIPID CONJUGATES AND METHODS OF PREPARING SAME

CROSS-REFERENCE TO RELATED APPLICATIONS

This application is a national phase application under 35 U.S.C. § 371 of International Application No. PCT/CA2016/000114 filed 14 Apr. 2016, which claims priority to U.S. Provisional Application No. 62/148,839 filed 17 Apr. 2015. The entire contents of each of the above-referenced disclosures is specifically incorporated by reference herein without disclaimer.

FIELD OF THE INVENTION

The invention relates to the field of texaphyrin derivatives, and, more specifically, to texaphyrin-phospholipid conjugates and applications and methods thereof.

BACKGROUND OF THE INVENTION

Texaphyrins, pentaaza Schiff base macrocycles, share a strong, but 'expanded', similarity to porphyrins and derivatives. Discovered decades ago,[1] texaphyrins have exhibited a variety of attractive intrinsic properties. With demonstrated capabilities of forming stable 1:1 complexes with a wide range of metal cations (particularly trivalent lanthanides), applications of texaphyrins were observed in cancer therapy and imaging.[2] Absorbing strongly in the tissue-transparent 700-900 nm range, texaphyrins offer a unique capability of in vivo excitation through external photon sources. In addition to these properties, texaphyrins exhibit inherent selective biolocalization in certain tissues, as well as having selectivity to tumours.

Efforts have been made to enhance the efficacy and selectivity of texaphyrins through conjugation methodologies. One such example is the use of texaphyrin as a "carrier" to overcome platinum drug resistance in cancer therapy,[3] involving the conjugation of texaphyrin to platinum drugs (i.e. cisplatin), through covalent linkage at the benzylic position. Moreover, lipophilic molecules have been conjugated with texaphyrins in an effort to incorporate into a biological vesicle.[4]

Conjugation of biologically active compounds to texaphyrins serve several benefits: i) the intrinsic tumour selectivity of texaphyrins can reduce aspecific toxicity of certain drugs; ii) addition of hydrophilic units can aid in the water solubility of texaphyrins, thereby increasing bioavailability; and iii) conjugation of texaphyrin to a targeting moiety can increase localization and accumulation in target tissues. Exploring novel texaphyrin conjugates offers an avenue into building upon demonstrated therapeutically relevant properties of texaphyrins, in applications pertaining to cancer therapy and imaging.

SUMMARY OF INVENTION

In accordance with one aspect, there is provided a texaphyrin-phospholipid conjugate comprising a texaphyrin, texaphyrin derivative or texaphyrin analogue covalently attached to a glycerol moiety of a phospholipid, in one embodiment, via a lipid side chain.

In accordance with a further aspect, there is provided a nanoparticle comprising the texaphyrin-phospholipid conjugates described herein.

In accordance with a further aspect, there is provided methods for preparing the texaphyrin-phospholipid conjugates described herein.

In accordance with a further aspect, there is provided use of the texaphyrin-phospholipid conjugates or nanoparticles described herein for photoacoustic imaging, photodynamic therapy, photothermal therapy or fluorescence imaging.

BRIEF DESCRIPTION OF FIGURES

Embodiments of the invention may best be understood by referring to the following description and accompanying drawings. In the drawings.

DETAILED DESCRIPTION

Figure 1:
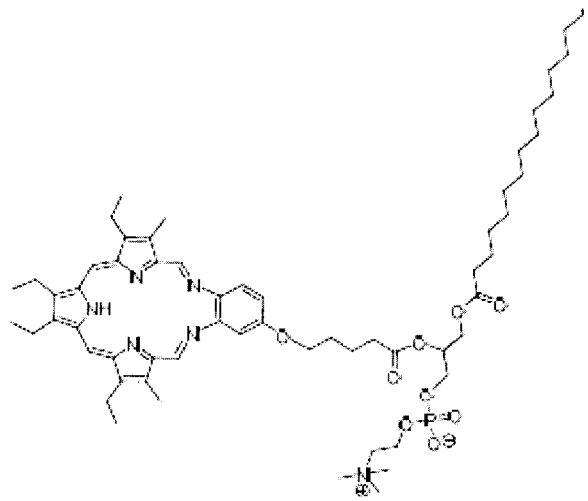
FIG. 1 shows characterizations for free-base texaphyrin-lipid conjugate. A. Photodiode array spectrum (range from 200-800 nm). B. High-resolution mass spectrometry, indicating M+Z and corresponding fragmentation pattern.
Figure 1:
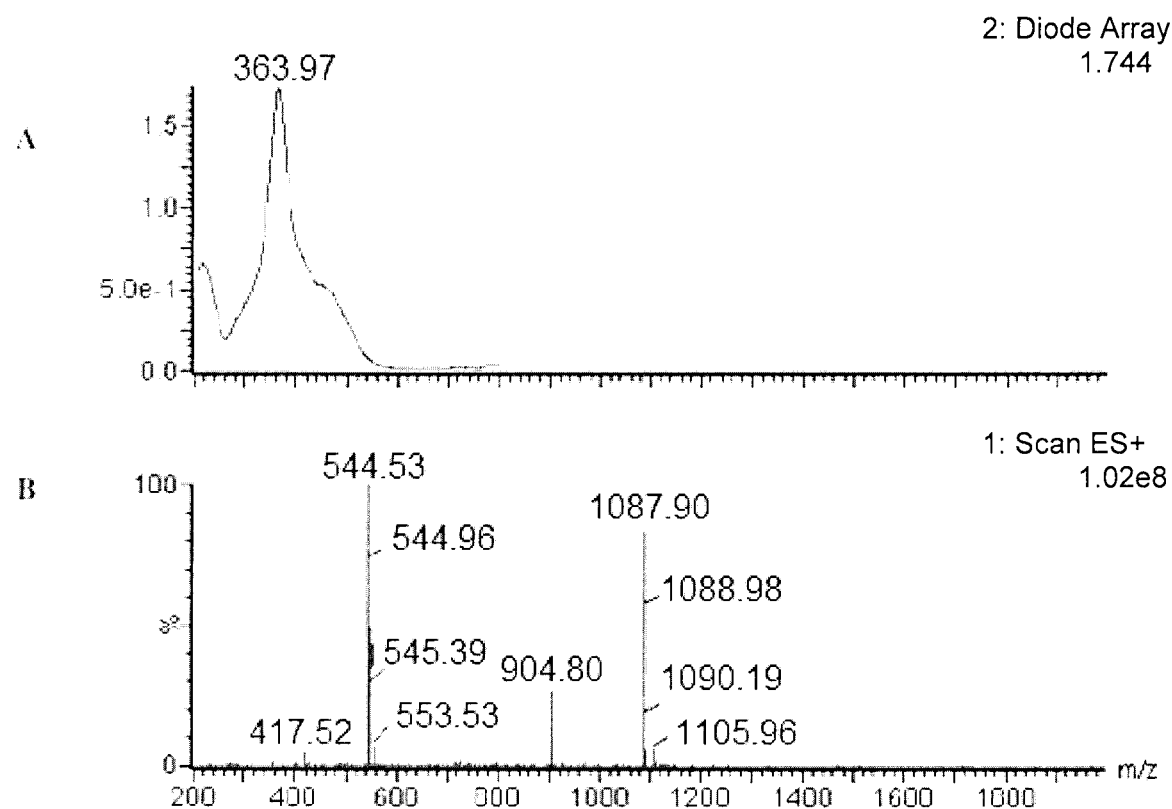

The present invention describes the preparation of a new molecular entity, a texaphyrin-phospholipid. While lipophilic molecules have been conjugated onto texaphyrins previously, this invention represents a novel class of compound, using a rational synthetic approach. The texaphyrin-phospholipid synthesis was strategically designed, and alternative methods of synthesis were eliminated as potential avenues through unsuccessful synthetic trials.

The general scheme for the synthesis of texaphyrin-phospholipid conjugates is based upon the formation of a central phenylenediamine conjugated to a phospholipid, which when reacted with tripyrranes, readily forms free base texaphyrin-phospholipid conjugates. This core moiety then has the potential to form known stable 1:1 complexes with a variety of metals: Mn, Fe, Co, Zn, Y, Cd, In, Bi, Sm, Eu, Gd, Tb, Dy, Ho, Er, Tm, Yb, and Lu.

Depending on the choice of metal, the molecule can be fine-tuned for specific biomedical applications. This invention includes all texaphyrin-phospholipid structures, as well as their metal-coordinated counterparts.

According to one aspect, there is provided a texaphyrin-phospholipid conjugate, wherein the texaphyrin-phospholipid conjugate comprises a texaphyrin, texaphyrin derivative or texaphyrin analog covalently attached to a lipid side chain of a phospholipid.

Texaphyrin is a sub-class of heterocyclic molecules known as porphyrins, and has a core moiety as illustrated in Formula I below. Some of the texaphyrin molecules have a shape that can superimpose onto the points of a star. As used herein, "texaphyrin, texaphyrin derivative or texaphyrin analog" refers to a molecule having a core moiety represented by Formula I. Example texaphyrin, texaphyrin derivative or texaphyrin analogs are described in U.S. Pat. Nos. 5,162,509; 6,207,660; 4,935,498 and 6,375,930, all of which are incorporated herein by reference.

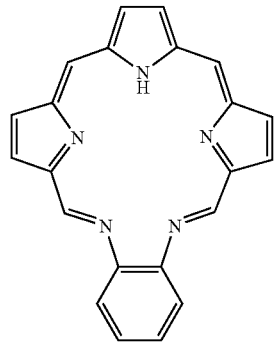

Formula I

In preferred embodiments, the texaphyrin, texaphyrin derivative or texaphyrin analog is covalently attached to a lipid side chain of a phospholipid at the sn-1 or the sn-2 position.

As used herein, "phospholipid" is a lipid having a hydrophilic head group having a phosphate group and a hydrophobic lipid tail. The hydrophilic head group and the hydrophobic lipid tail are joined together by a glycerol molecule.

Exemplary phospholipids include, but are not limited to, phosphatidylcholine, phosphatidylethanoloamine, phosphatidylserine, and phosphatidylinositol. In some embodiments, the phospholipid comprises an acyl side chain of 12 to 22 carbons.

In other embodiments, the texaphyrin, texaphyrin derivative or texaphyrin analog is conjugated to the glycerol group on the phospholipid by a carbon chain linker of 0 to 20 carbons.

The core moiety of texaphyrins has the potential to form known stable complexes with a variety of metals. Exemplary metals to which the texaphyrin-phospholipid conjugate is complexed include, but are not limited to, Mn, Fe, Co, Zn, Y, Cd, In, La, Hg, Pb, Bi, Ce, Pr, Nd, Sm, Eu, Gd, Tb, Dy, Ho, Er, Tm, Yb, and Lu.

Nanoparticles

The texaphyrin-phospholipid conjugate described above can be assembled into nanoparticles. According to a further aspect, there is provided a nanoparticle comprising this texaphyrin-phospholipid conjugate. Such nanoparticles may comprise at least 15, 25, 35, 45, 55, 65, 75, 85, 95 or 100 molar % conjugate.

In some embodiments, the nanoparticles further comprises PEG phospholipids, PEG lipids, and/or PEG-DSPE. In further embodiments, these PEG, PEG-lipid, or PEG-DSPE is present in the nanoparticle in an amount of about 5 molar %. The remainder of the nanoparticle may be comprised of unconjugated phospholipids.

The nanoparticle can be a bilayered vesicle or a monolayered vesicle. In some embodiments, the nanoparticle is substantially spherical and between about 3 nm and about 200 nm in diameter. In more preferred embodiments the nanovesicle is substantially spherical and between about 100 nm and about 120 nm in diameter.

In other embodiments, the nanoparticle further comprises an active agent encapsulated therein. Preferably the active agent is a therapeutic agent or a diagnostic agent. More preferably, the active agent is a chemotherapy agent such as, but not limited to, a taxane or doxorubicin.

The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

A "diagnostic" or "diagnostic agent" is any chemical moiety that may be used for diagnosis. For example, diagnostic agents include imaging agents, such as those containing radioisotopes such as indium or technetium; contrasting agents containing iodine or gadolinium; enzymes such as horse radish peroxidase, GFP, alkaline phosphatase, or β-galactosidase; fluorescent substances such as europium derivatives; luminescent substances such as N-methylacrydium derivatives or the like.

In yet other embodiments, the nanoparticle further comprises targeting molecules. Preferably the targeting molecule is an antibody, peptide or aptamer.

"Targeting molecule" is any molecule that can direct the nanovesicle to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, or single chain, many of which are commercially available or readily obtained using standard techniques.

Methods

According to a further aspect, there is provided a method of preparing the texaphyrin-phospholipid conjugate as described above, comprising reacting

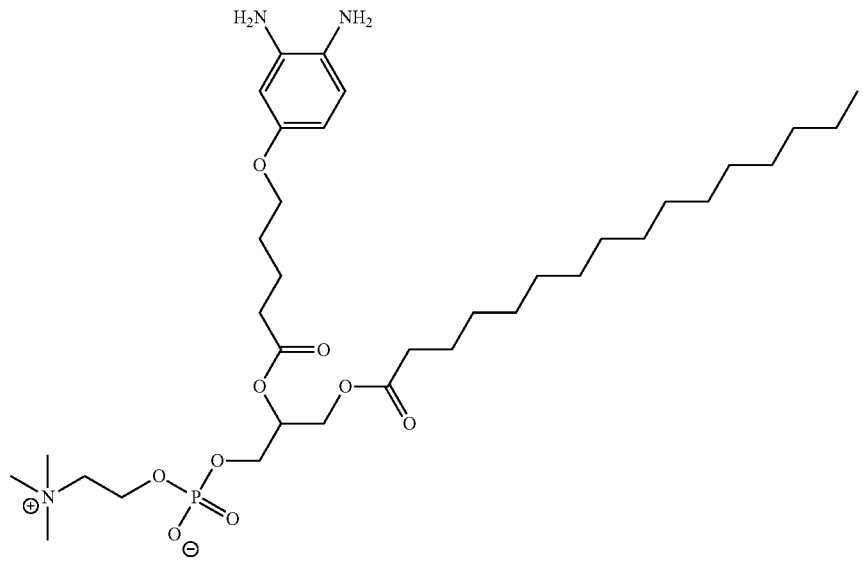

6 with

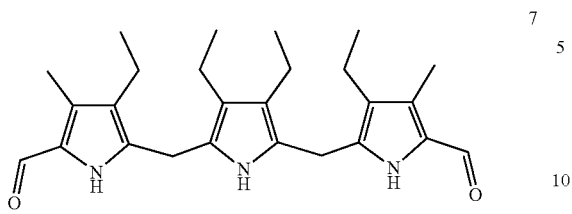

to yield

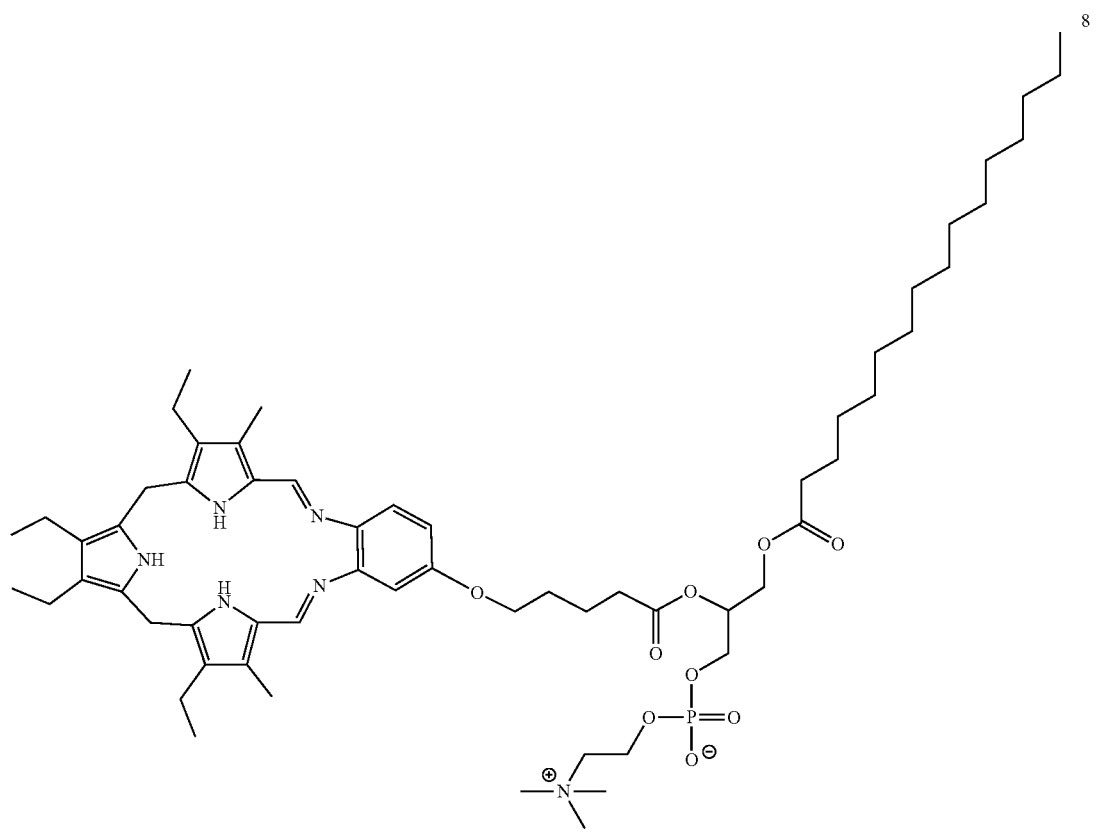 [SMILES: CCCCCCCCCCCCCCCC(=O)OCC(COP(=O)([O-])OCC[N+](C)(C)C)OC(=O)CCCCOc1ccc2c(c1)/N=C/c1[nH]c(c(CC)c1C)Cc1[nH]c(c(CC)c1CC)Cc1[nH]c(c(C)c1CC)/C=N/2]

under suitable reaction conditions. Optionally, compounds 6, 7, and 8 can be substituted as necessary. Compounds 6 and 7 can be optionally substituted to yield compound 8 or a texaphyrin-phospholipid conjugate having a desired texaphyrin, texaphyrin derivative or texaphyrin analog, including those described in any of U.S. Pat. Nos. 5,162,509; 6,207,660; 4,935,498 and 6,375,930.

For example, compounds 6, 7, and 8 may have the general formulas below.

Compound 6

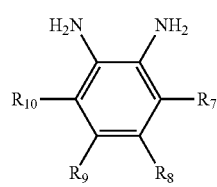

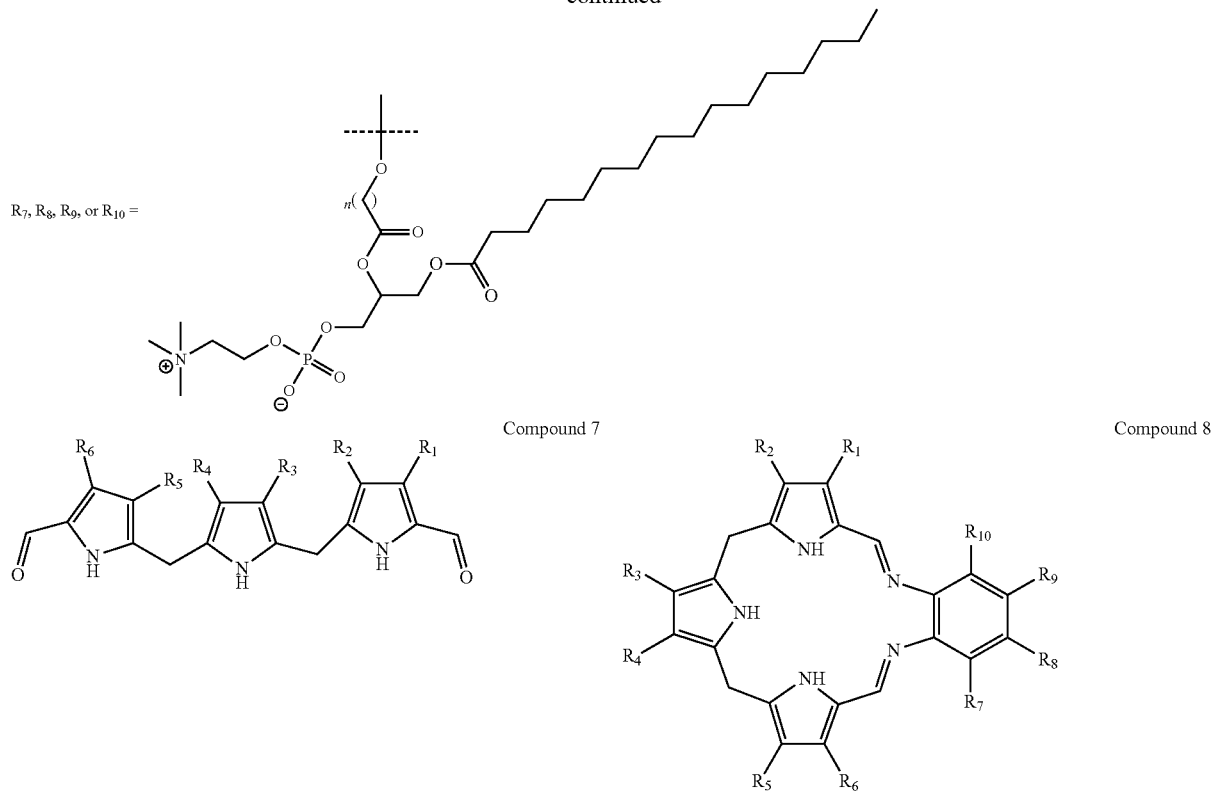

One of $R_7$-$R_{10}$ will possess the phospholipid conjugation as exemplified above with respect to compound 6. The remainder of $R_7$-$R_{10}$ may be independently selected from H, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, and an acyl group. Preferably the $R_7$-$R_{10}$ group, other than the phospholipid, comprises 1-4 carbons.

$R_1$-$R_6$ are each independently selected from the group consisting of H, an alkyl group, or an alkyl group with substituted with an OH, SH, heteroalkyl, aryl, heteroaryl, or heterocyclic group. For example, $R_1$-$R_6$ may be selected to improve water solubility or favourable stacking interactions in the nanoparticle membrane. Preferably, the alkyl will be a lower $C_{1-4}$ alkyl.

n is an integer, preferably 1, 2, 3, 4, 5, 6, 7, 8, 9, or 10.

The phospholipid in compounds 6 and 8 may be replaced as desired with any suitable phospholipid, including but not limited to those described above.

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "organic group" means a group containing at least one carbon atom.

The term "alkyl group" means a group formed by removing a hydrogen from a carbon of an alkane, where an alkane is an acyclic or cyclic compound consisting entirely of hydrogen atoms and saturated carbon atoms. An alkyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "heteroalkenyl group" means a group formed by removing a hydrogen from a carbon of a heteroalkene, where a heteroalkene is an acyclic or cyclic compound consisting entirely of hydrogen atoms, carbon atoms and one or more heteroatoms, and including at least one carbon-carbon double bond. A heteroalkenyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "heteroalkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "aryl group" means a group formed by removing a hydrogen from a ring carbon atom of an aromatic hydrocarbon. An aryl group may by monocyclic or polycyclic and may include one or more substituent groups.

The term "heteroaryl group" means a group formed by replacing one or more methine (—C=) and/or vinylene (—CH=CH—) groups in an aryl group with a trivalent or divalent heteroatom, respectively. A heteroaryl group may by monocyclic or polycyclic and may include one or more substituent groups.

The term "substituent group" means a group that replaces one or more hydrogen atoms in a molecular entity.

The term "heterocyclic group" means a group formed by removing a hydrogen from a cyclic compound that has atoms of at least two different elements as members of its ring(s).

The term "acyl group" means a group formed by removing one or more hydroxyl groups from an oxoacid, i.e. RCO—.

According to a further aspect, there is provided a method of preparing

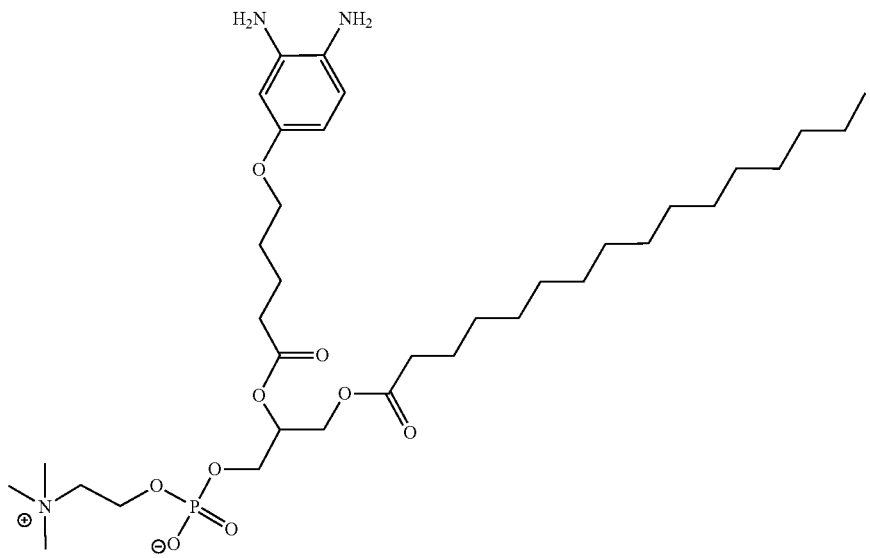

6 by reducing

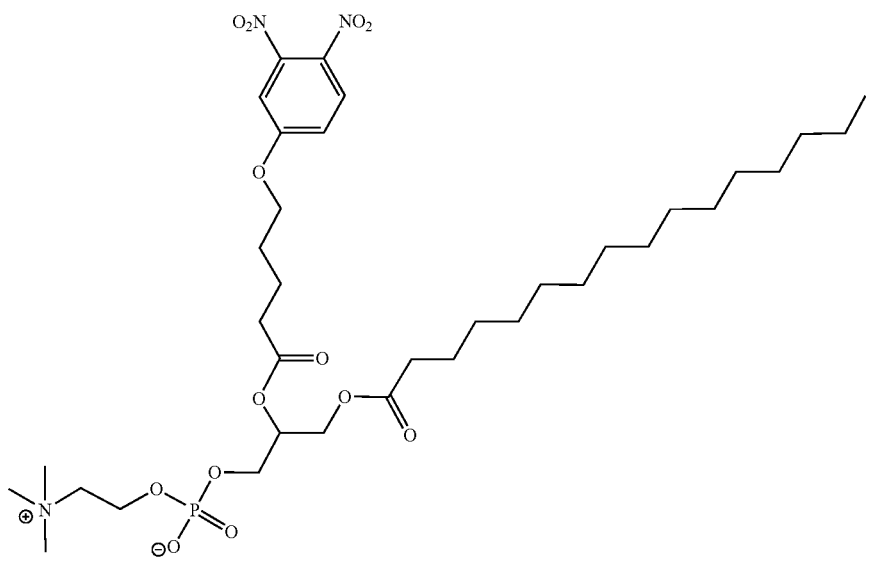

5 under suitable reaction conditions. Optionally, any of compounds 5 and 6 can be substituted as necessary to yield compound 8 or a texaphyrin-phospholipid conjugate having a desired texaphyrin, texaphyrin derivative or texaphyrin analog, including those described in any of U.S. Pat. Nos. 5,162,509; 6,207,660; 4,935,498 and 6,375,930, when additionally performing the method of preparing texaphyrin-phospholipid conjugate as described above.

Accordingly, compound 5 may have the general formula below.

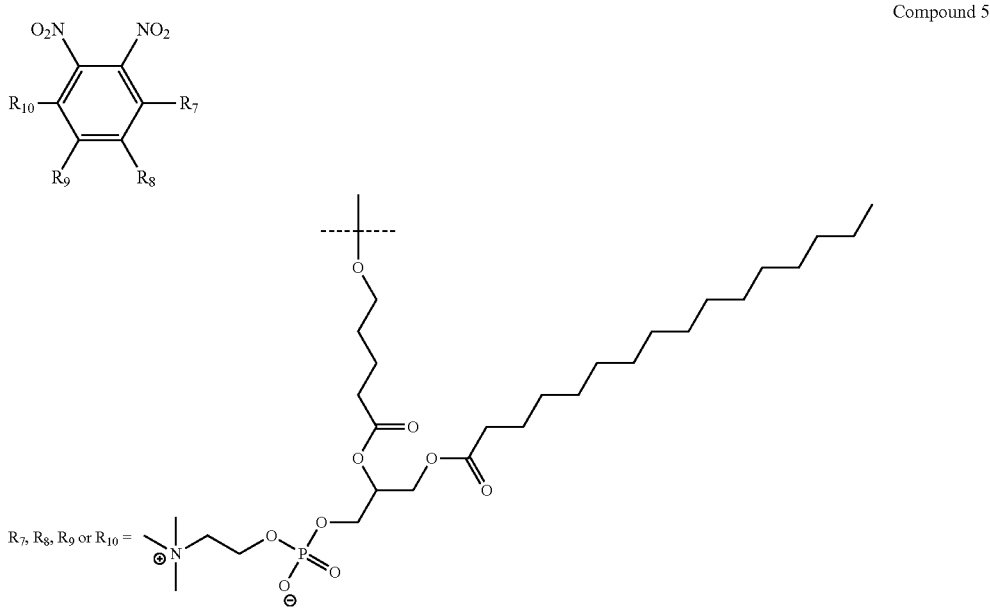

Compound 5

One of $R_7$-$R_{10}$ will possess the phospholipid conjugation as exemplified above. The remainder of $R_7$-$R_{10}$ may be.

The phospholipid in compounds 5 and 6 may be replaced as desired with any suitable phospholipid, including but not limited to those described above. Compound 6, or 2-((5-(3,4-Diaminophenoxy)pentanoyl)oxy)-3-(palmitoyloxy)propyl (2-trimethylammonio)ethyl) phosphate is prepared by this method.

According to a further aspect, there is provided a method of preparing

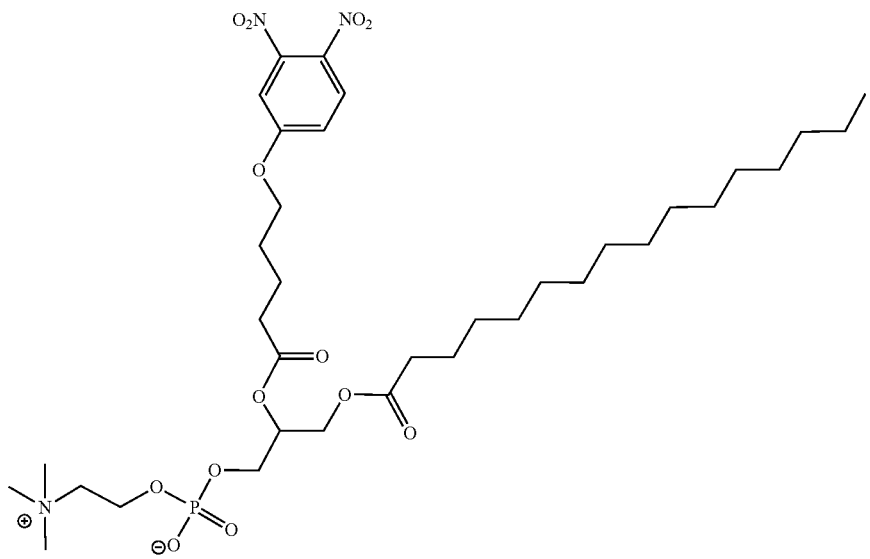

5 by reacting

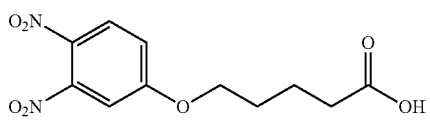

with

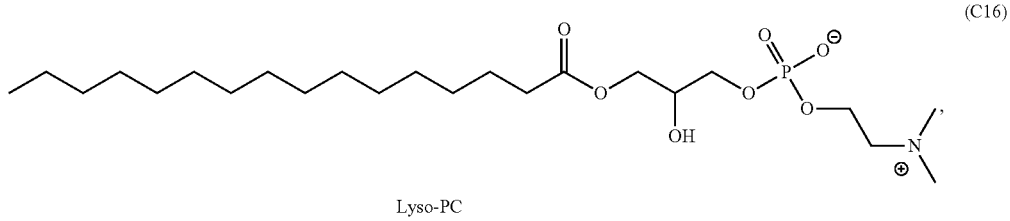 [SMILES: CCCCCCCCCCCCCCCC(=O)OCC(O)COP(=O)([O-])OCC[NH+](C)C]

Lyso-PC under suitable reaction conditions.

Optionally, compound 4 can be substituted as necessary to yield compound 8 or a texaphyrin-phospholipid conjugate having a desired texaphyrin, texaphyrin derivative or texaphyrin analog, including those described in any of U.S. Pat. Nos. 5,162,509; 6,207,660; 4,935,498 and 6,375,930, when additionally performing the methods as described above.

Accordingly, compound 4 may have the general formula below.

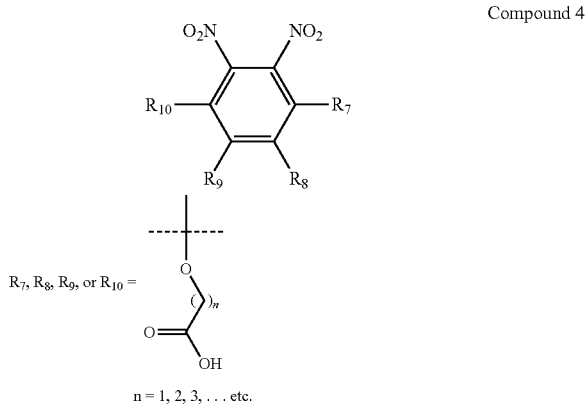

Compound 4

One of $R_7$-$R_{10}$ will comprise the linker to which the phospholipid will be conjugated. The remainder of $R_7$-$R_{10}$ may be as described above.

As noted previously, may be replaced as desired with any suitable phospholipid, including but not limited to those described above. Compound 5, or 2-((5-(3,4-Dinitrophenoxy)pentanoyl)oxy)-3-(palmitoyloxy)propyl (2-(trimethylammonio)ethyl) phosphate is prepared by this method.

According to a further aspect, there is provided a method of synthesizing a texaphyrin, texaphyrin derivative or texaphyrin analog, comprising cleaving the texaphyrin, texaphyrin derivative or texaphyrin analog from the texaphyrin-phospholipid conjugate described above. In some embodiments, the texaphyrin-phospholipid conjugate prepared by the methods described above is cleaved. In other embodiments, the cleaving is performed using an enzyme. Preferably, a cleaving enzyme as described in WO 2012/167350, incorporated herein by reference, is used.

Uses

According to a further aspect, there is provided use of the texaphyrin-phospholipid conjugate or nanoparticle as described above for photoacoustic imaging, photodynamic therapy, photothermal therapy or fluorescence imaging.

According to a further aspect, there is provided use of the texaphyrin-phospholipid conjugate or nanoparticle as described above for magnetic resonance imaging.

The following examples are illustrative of various aspects of the invention, and do not limit the broad aspects of the invention as disclosed herein.

EXAMPLES

General architecture of texaphyrin-phospholipid conjugates and the incorporation of metal ion of choice is depicted in the scheme below. See FIG. 1 for characterization of a texaphyrin-lipid conjugate.

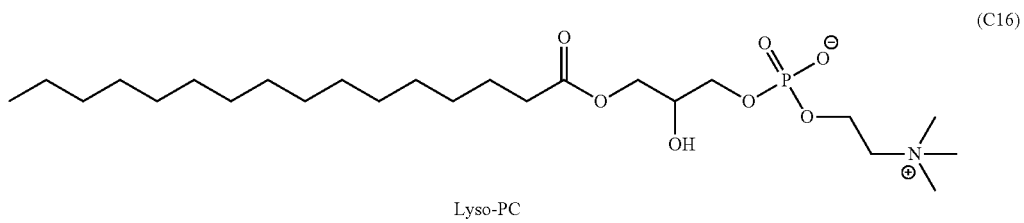 [SMILES: CCCCCCCCCCCCCCCC(=O)OCC(O)COP(=O)([O-])OCC[N+](C)(C)C]

Lyso-PC

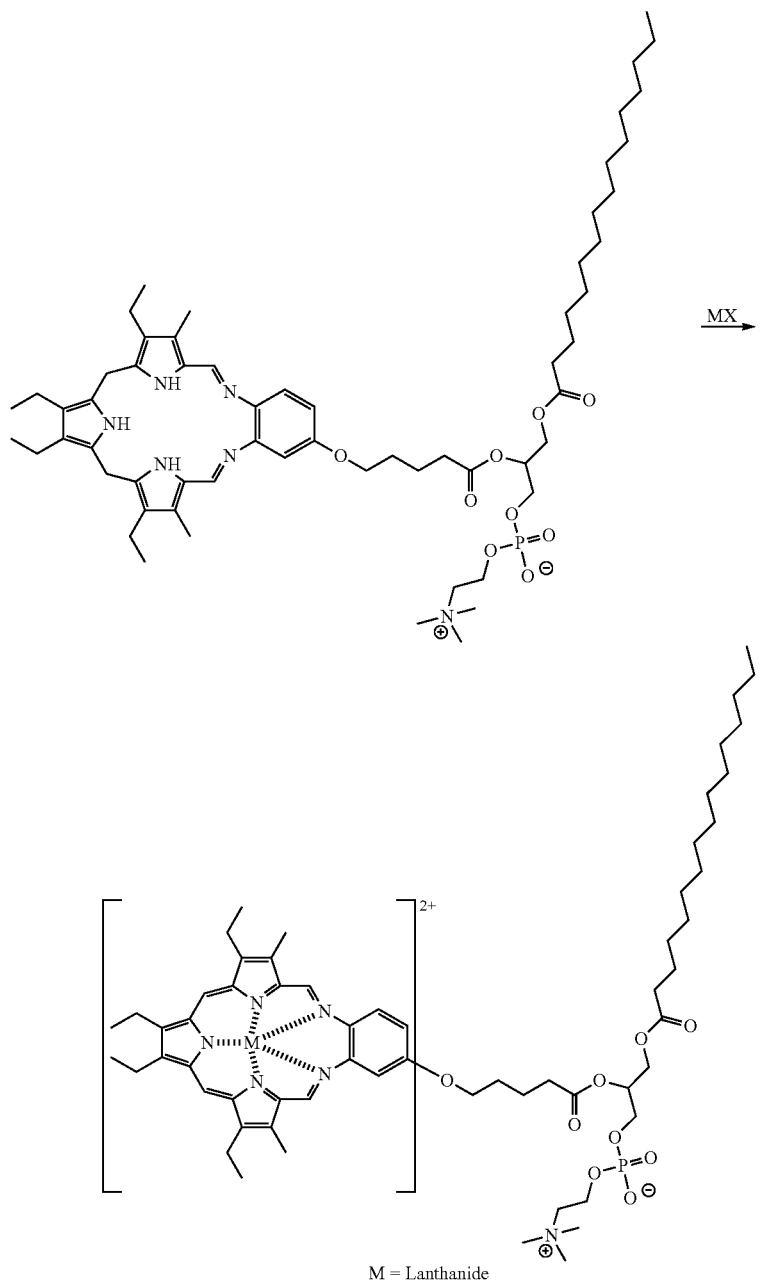

M = Lanthanide

The synthetic route designed eliminated possible alternative strategies, eluding to the necessity of forming a central phenylenediamine conjugated to a phospholipid. Attempts were made forming texaphyrins with exocyclic carboxylates, to attempt coupling conjugations with a variety of phospholipids in varying conditions and synthetic strategies. It was unequivocally determined that this strategy is ineffective at forming texaphyrin-phospholipid conjugates.

Texaphyrin-phospholipid conjugates described herein include phospholipids with varying alkyl chain length (n=1, 2, 3, etc.), branching (—OH, —SH, —OMe, etc.), unsaturation, and geometry.

Synthesis Scheme of Texaphyrin-Phospholipid Conjugate:

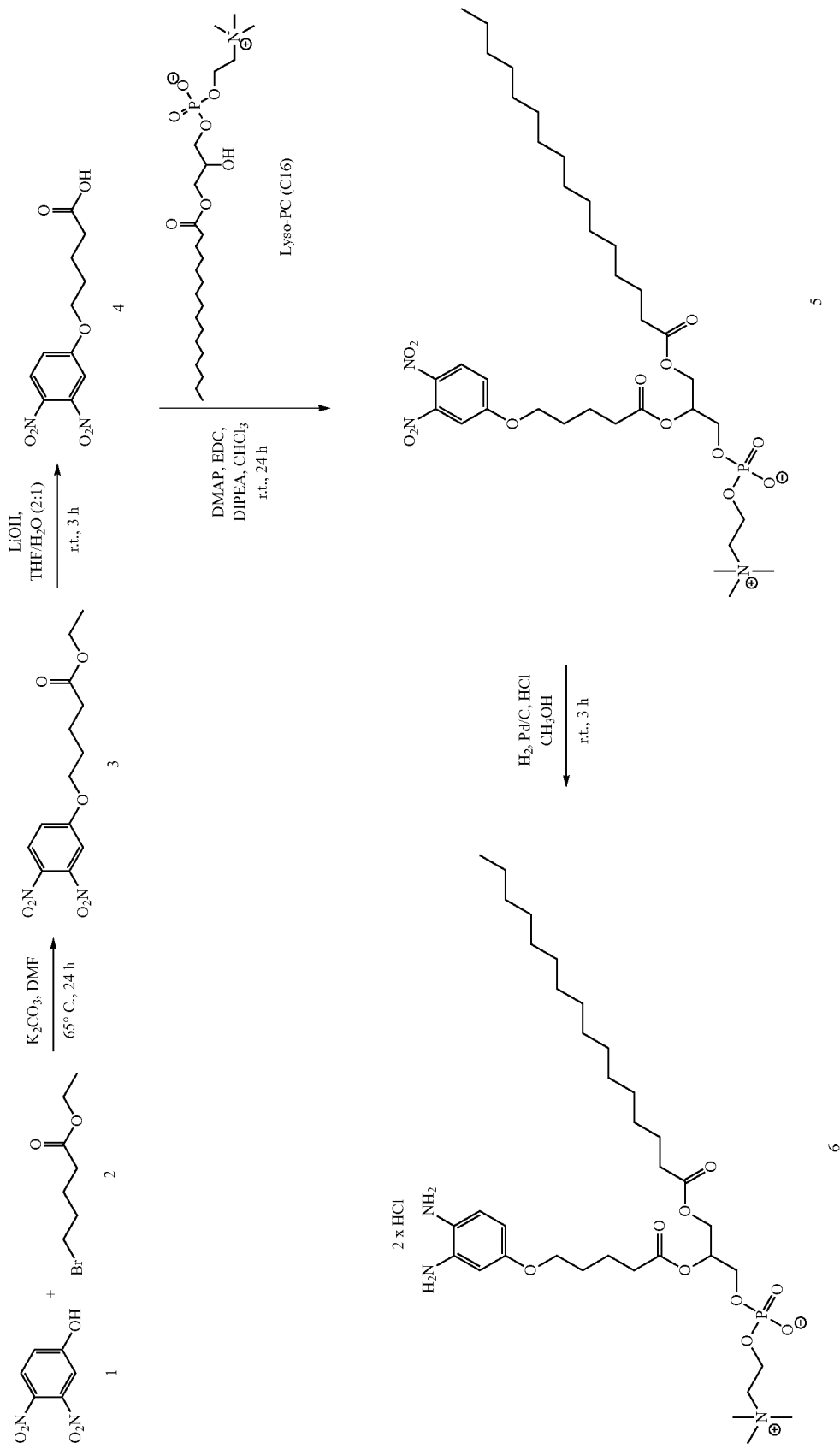

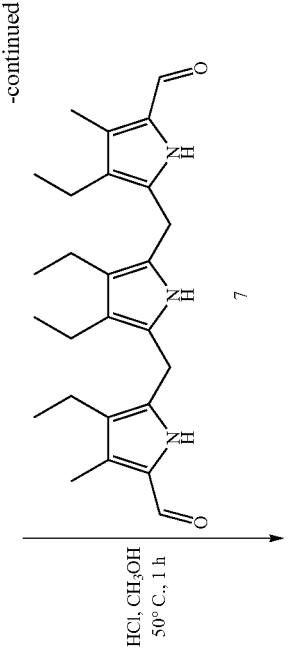
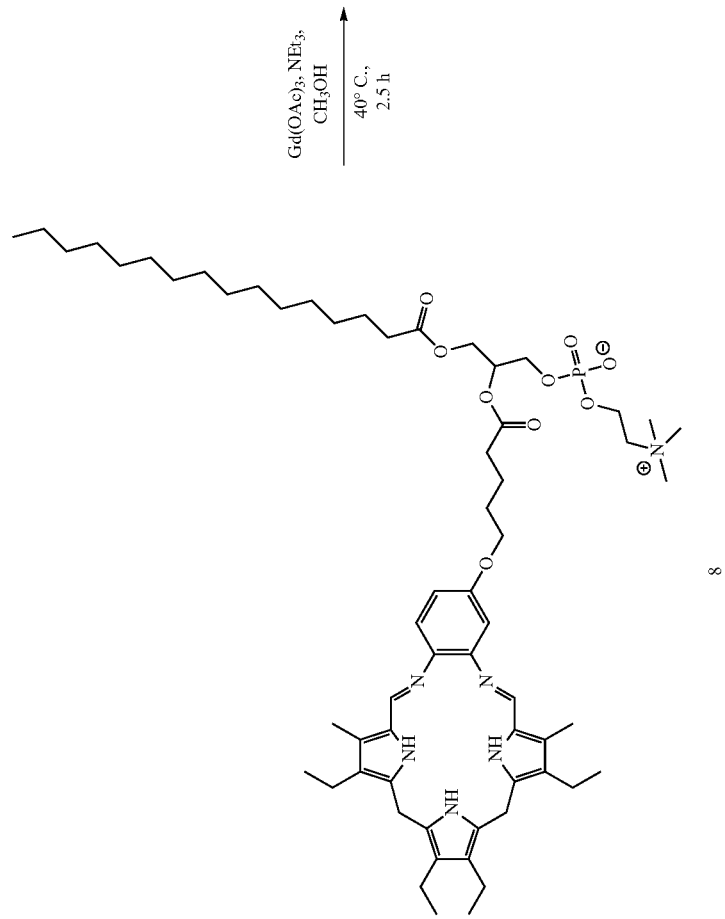

Ethyl 5-(3,4-dinitrophenoxy)pentanoate (3)

To a reaction vessel is added 3,4-dinitrophenol (4.58 g, 24.87 mmol) and K2CO3 (5.16 g, 37.31 mmol), in 15 mL of anhydrous DMF. Next, at 0° C. is added ethyl-5-bromovalerate (4.33 mL, 27.36 mmol) drip-wise, and the reaction is allowed to stir at 65° C. for 24 hours. Once complete, water (50 mL) is added, and extracted with ethyl acetate (3×35 mL). The organic layers are combined, washed with water (35 mL), saturated sodium bicarbonate solution (2×25 mL), brine (25 mL), dried over MgSO$_4$, filtered, and condensed in vacuo to afford 3 as a yellow solid: 7.2 g, 94% yield; $^1$H NMR (CDCl$_3$) δ 8.06 (d, J=1.0 Hz, 1H), 7.21 (d, J=2.8 Hz, 1H), 7.12 (dd, J=9.0, 2.8 Hz, 1H), 4.11-4.18 (m, 4H), 2.41 (t, J=1.0 Hz, 2H), 1.80-1.95 (m, 4H), 1.26-1.30 (m, 3H); $^{13}$C NMR (CDCl$_3$) δ 163.0, 127.5, 117.0, 110.7, 69.4, 60.5, 33.6, 32.0, 28.1, 23.5, 21.3, 14.2.

5-(3,4-Dinitrophenoxy)pentanoic Acid (4)

To an RBF is charged with 3 (5.68 g, 18.18 mmol) and lithium hydroxide (870.94 mg, 36.37 mmol) in 20 mL of a 2:1 THF/H$_2$O solution. After 3 h, solvent is completely removed, and water (10 mL) is added to the residue. The vessel is then placed on an ice bath, and acidified to pH 3 with 1M HCl. The mixture is subsequently extracted with ethyl acetate (3×25 mL), combined, dried over MgSO$_4$, filtered, and condensed under reduced pressure to afford 4 as a light yellow solid: 5.17 g, quantitative; $^1$H NMR (CDCl$_3$) δ 8.05 (d, J=9.0 Hz, 1H), 7.21 (d, J=2.8 Hz, 1H), 7.12 (dd, J=9.0, 2.5 Hz, 1H), 4.14 (t, J=5.9 Hz, 2H), 2.48 (t, J=7.0 Hz, 2H), 2.06 (s, 1H), 1.82-1.98 (m, 8H)

2-((5-(3,4-Dinitrophenoxy)pentanoyl)oxy)-3-(palmitoyloxy)propyl (2-(trimethylammonio)ethyl) phosphate (5)

A reaction vessel is charged with 4 (450 mg, 1.58 mmol), 1-palmitoyl-2-hydroxy-sn-glycero-3-phosphocholine (784.72 mg, 1.58 mmol), N,N-diisopropylethylamine (165.5 µL, 0.95 mmol), 4-dimethylaminopyridine (96.71 mg, 0.79 mmol), and N-(3-dimethylaminopropyl)-N'-ethylcarbodiimide hydrochloride (607 mg, 3.17 mmol) in 15 mL of anhydrous CHCl$_3$, and allowed to stir at room temperature for 24 h. Confirmation of complete product conversion was determined using LCMS analysis. After 24, the residue is directly added onto a 50 g flash chromatography silica gel column, and purified using an initial gradient of methanol:dichloromethane (0-25% over 10 minutes), followed by a second gradient of chloroform:methanol:water (35:14:1, isocratic over 15 minutes), affording 6 as a light yellow solid: 967.5 mg, 80% yield.

2-((5-(3,4-Diaminophenoxy)pentanoyl)oxy)-3-(palmitoyloxy)propyl (2-trimethylammonio)ethyl) phosphate (6)

To an RBF is added 5 (641 mg, 0.859 mmol), and palladium on carbon (91.5 mg, 85.9 µmol) in 10 mL of anhydrous methanol, followed by the addition of concentrated HCl (213.8 µL, 2.58 mmol). The reaction vessel is then sealed, and purged several times with hydrogen atmosphere, activating the palladium catalyst. Once complete, the reaction vessel is placed under hydrogen atmosphere for 3 hours at room temperature. Upon completion, confirmed by LCMS analysis, the mixture is filtered, and concentrating in vacuo to afford 6 as a light pink solid: 602 mg, 99% yield.

3-(Palmitoyloxy)-2-((5-((13,33,34,53-tetraethyl-14, 54-dimethyl-12H,31H,52H-7,9-diaza-1,3,5(2,5)-tripyrrola-8(1,2)-benzenacyclodecaphane-6,9- dien-84-yl)oxy) pentanoyl)oxy)propyl (2-(trimethylammonio)ethyl) phosphate (8)

To a reaction vessel is added 7 (226.7 mg, 0.538 mmol) and 6 (377.5 mg, 0.538 mmol) in 6 mL of anhydrous methanol, followed by the addition of concentrated HCl (89.2 µL, 1.08 mmol). The reaction vessel is then heated to 50° C. for 30 minutes, while being shielded from light. Upon completion, the solvent is completely removed under reduced pressure. The residue is then washed with hexanes (5×10 mL), removing hydrophobic colour impurities, affording 8 as a dark red solid: 573 mg, 98% yield.

Figure 3:
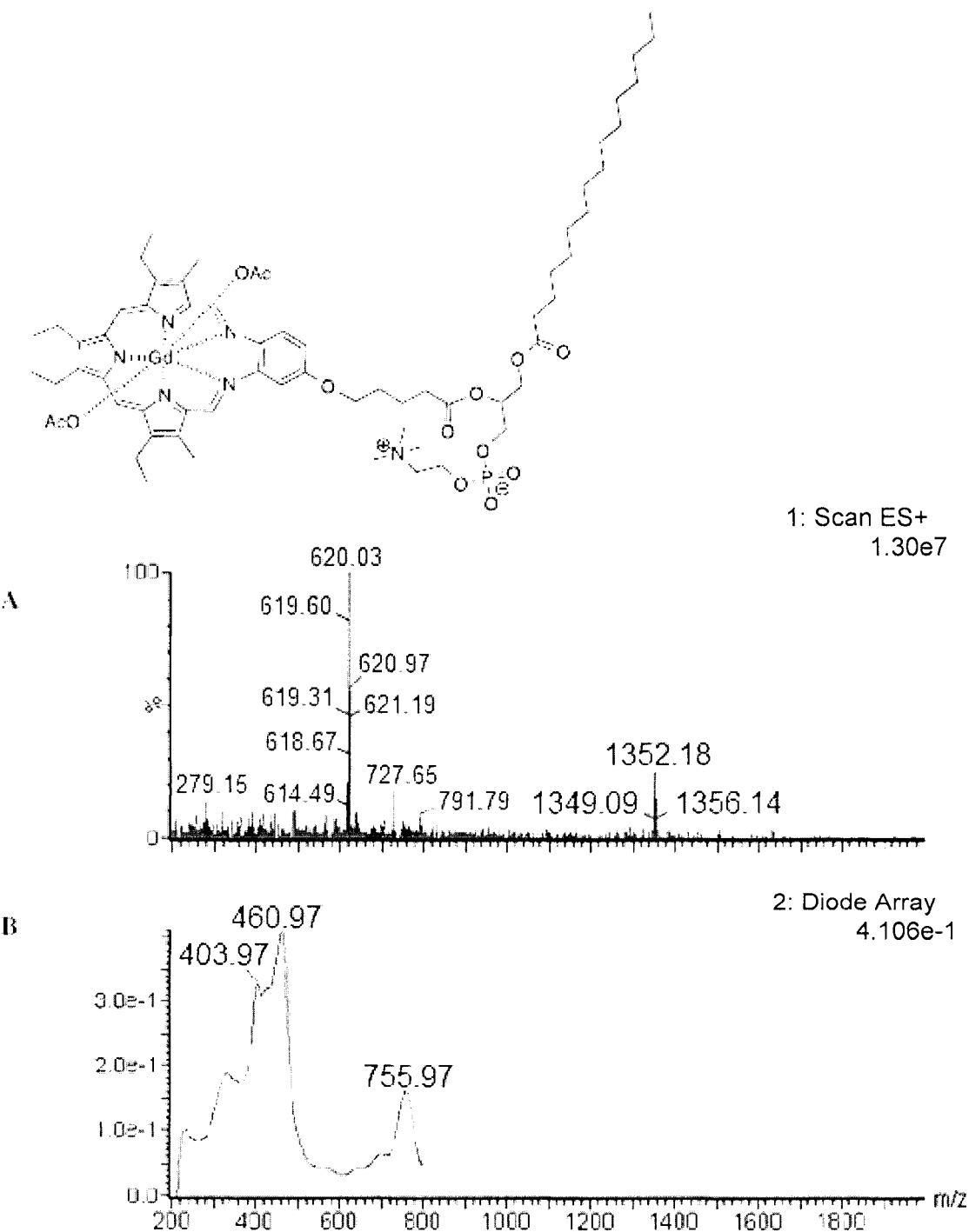
FIG. 3 shows characterizations for Gadolinium(III)-texaphyrin complex 9. A. High-resolution mass spectrometry, indicating M+Z and corresponding fragmentation pattern. B. Photodiode array spectrum (range from 200-800 nm).

Gadolinium(III) Complex 9 (see FIG. 3):

To a reaction vessel is added 8 (37.0 mg, 34.02 µmol), gadolinium(III) acetate hydrate (12.59 mg, 35.73 µmol), and triethylamine (47.43 µL, 340.25 µmol) in 4 mL of methanol, and allowed to stir open to air at 50°C for 3 hours. Once complete, the solvent is completely removed, and hexanes (3×10 mL) is added to the residue, removing light pink impurities to afford 9 as a dark green solid: 36.50 mg, 79% yield.

Figure 2:
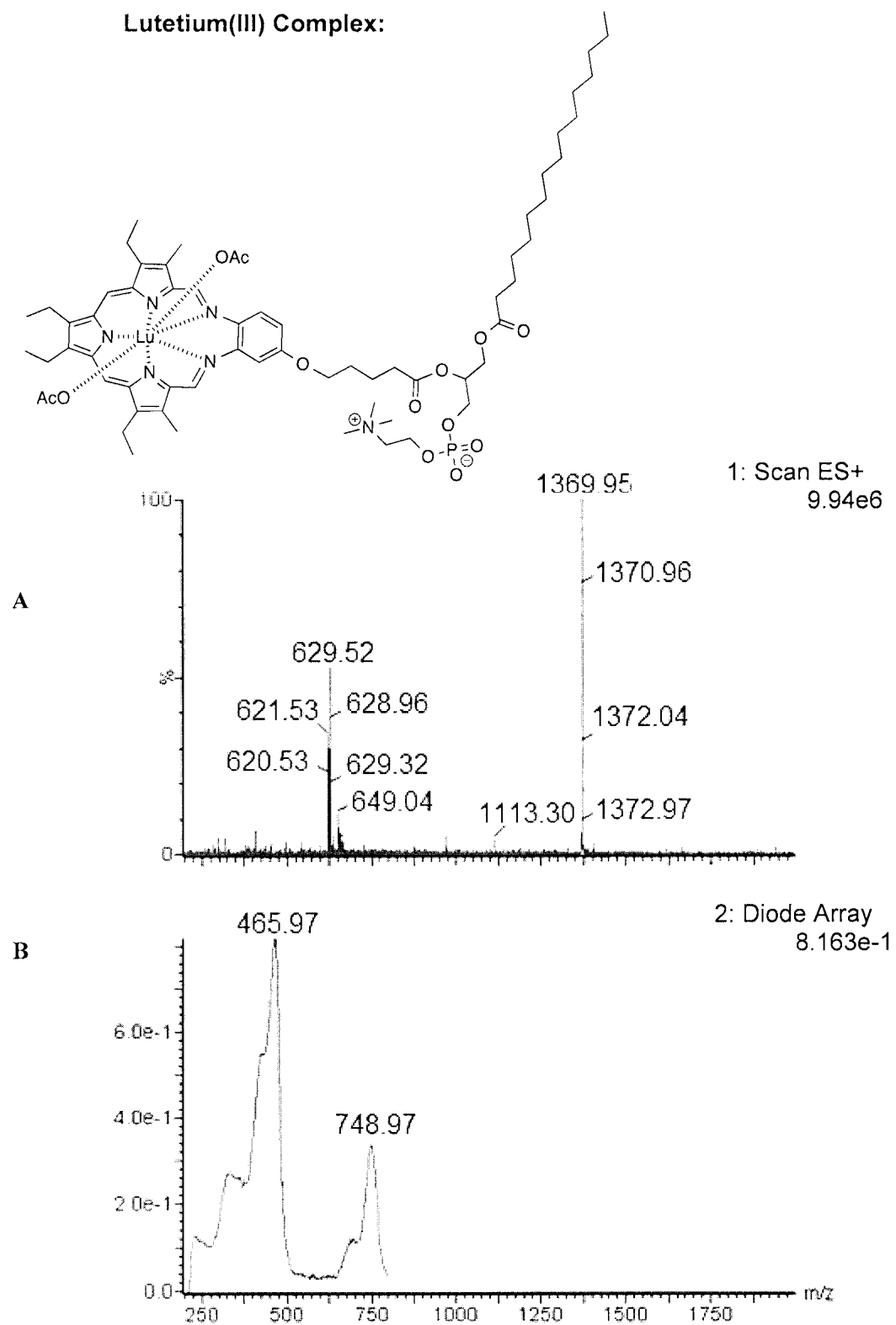
FIG. 2 shows characterizations for Lutetium(III)-texaphyrin complex. A. High-resolution mass spectrometry, indicating M+Z and corresponding fragmentation pattern. B. Photodiode array spectrum (range from 200-800 nm).

Lutetium(III) Complex (see FIG. 2):

To a reaction vessel is added 8 (25.0 mg, 23.00 µmol), lutetium(III) acetate hydrate (8.93 mg, 24.14 µmol), and triethylamine (32.04 µL, 229.90 µmol) in 5 mL of methanol, and allowed to stir open to air at 52°C for 1.5 hours. Once complete, the solvent is completely removed, and hexanes (3×10 mL) is added to the residue, removing light pink impurities to afford Lutetium (III) complexed texaphyrin-lipid as a dark green solid: 19.83 mg, 63% yield.

Figure 4:
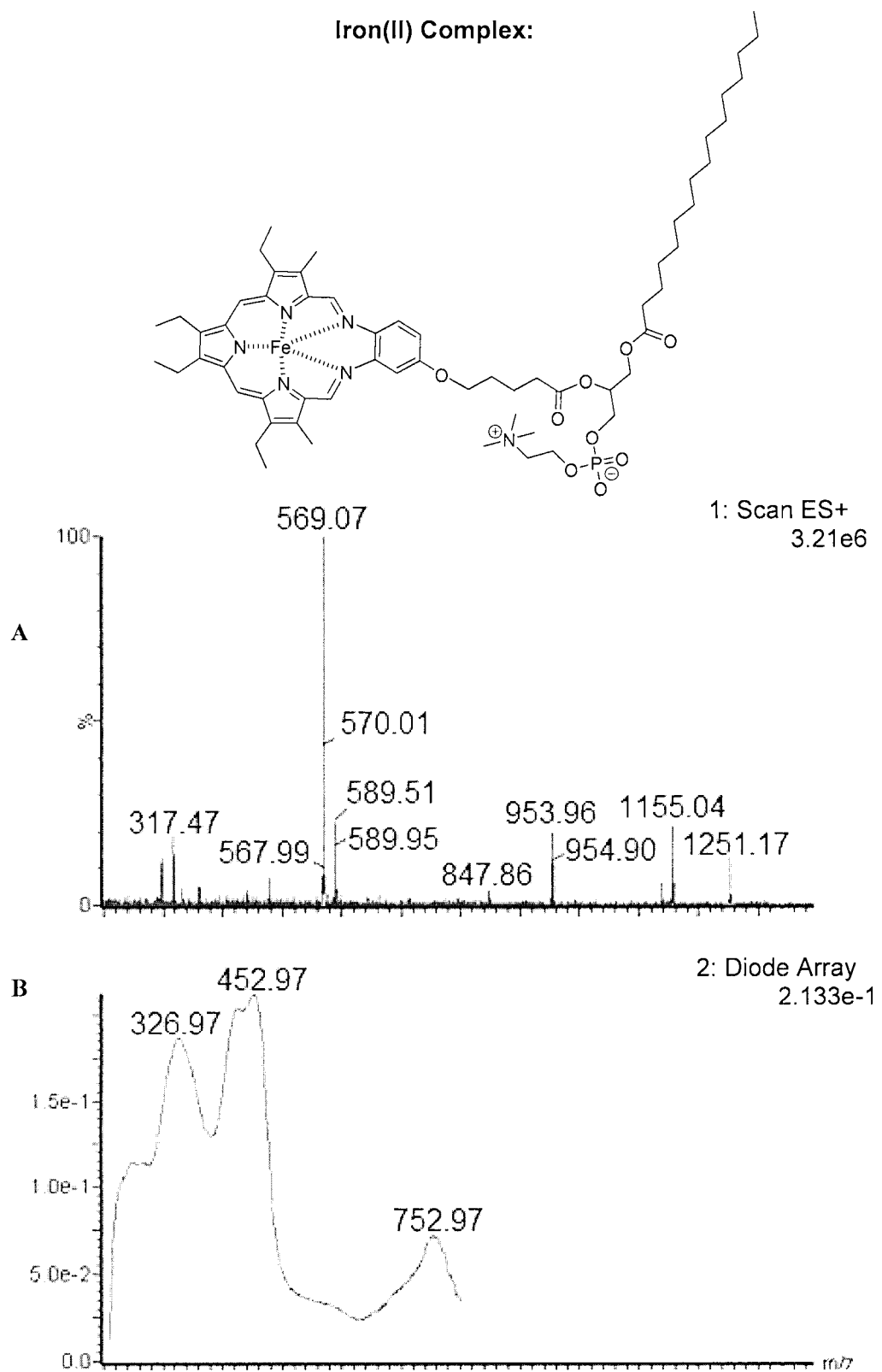
FIG. 4 shows characterizations for Iron(II)-texaphyrin complex. A. High-resolution mass spectrometry, indicating M+Z and corresponding fragmentation pattern. B. Photodiode array spectrum (range from 200-800 nm).

Iron(II) Complex (see FIG. 4):

To a reaction vessel is added 8 (17.0 mg, 15.63 µmol), iron(II) acetate (3.15 mg, 16.41 µmol), and triethylamine (21.79 µL, 156.33 µmol) in 5 mL of methanol, and allowed to stir open to air at 52°C for 1 hour and 15 minutes. Once complete, the solvent is completely removed, and hexanes (3×10 mL) is added to the residue, removing light pink impurities to afford iron(II) complexed texaphyrin-lipid as a dark green solid: 13.5 mg, 69% yield.

Figure 5:
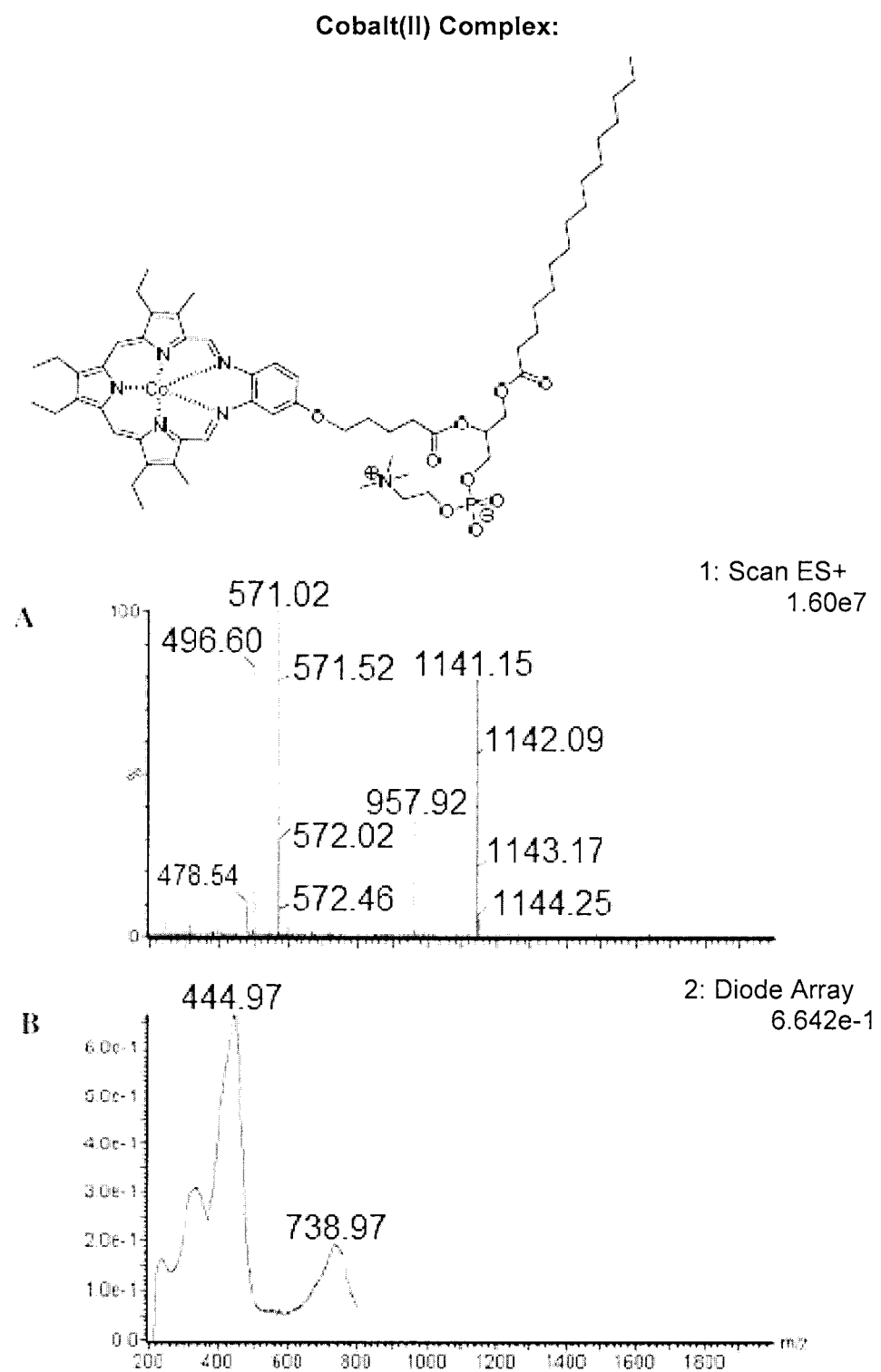
FIG. 5 shows characterizations for Cobalt(II)-texaphyrin complex. A. High-resolution mass spectrometry, indicating M+Z and corresponding fragmentation pattern. B. Photodiode array spectrum (range from 200-800 nm).

Cobalt(II) Complex (see FIG. 5):

To a reaction vessel is added 8 (15.0 mg, 13.79 µmol), cobalt(II) acetate (2.82 mg, 14.48 µmol), and triethylamine (19.23 µL, 137.94 µmol) in 5 mL of methanol, and allowed to stir open to air at 52°C for 45 minutes. Once complete, the solvent is completely removed, and hexanes (3×10 mL) is added to the residue, removing light pink impurities to afford cobalt(II) complexed texaphyrin-lipid as a dark green solid: 14.1 mg, 81% yield.

Characterizations for a Manganese (II) Complex, Yttrium (III) Complex, Cadmium (III) Complex, Indium (III) Complex, Bismuth (III) Complex, Samarium (III) Complex, Europium (III) Complex, Terbium (III) Complex, Dysprosium (III) Complex, Holmium (III) Complex, Erbium (III) Complex, Thulium (III) Complex, Ytterbium (III) Complex, and Rhenium (II) Complex are shown in FIGS. 14 to 27.

Attempted Strategies:
Method 1 Reaction Scheme:

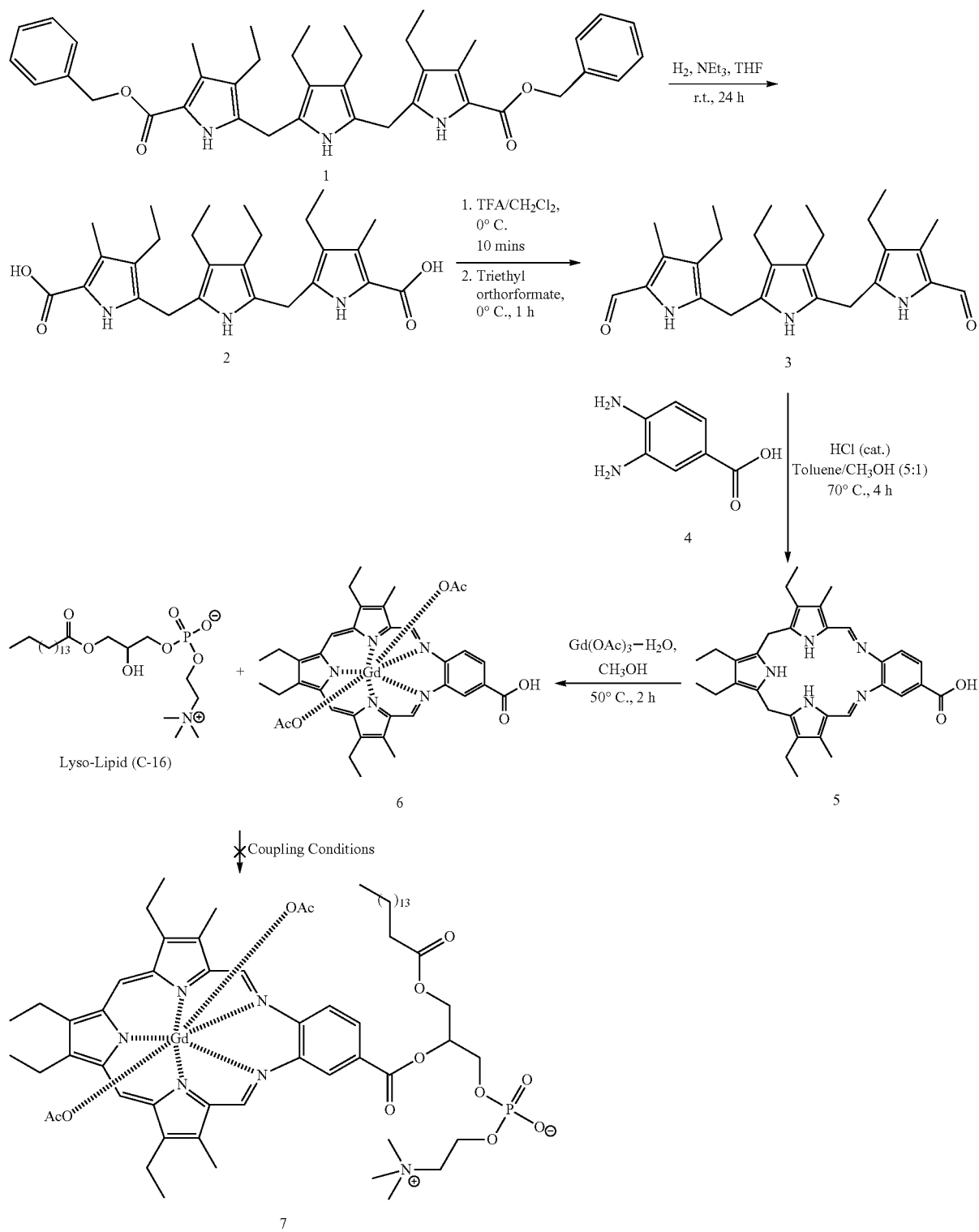

Initial synthetic efforts to afford a texaphyrin-phospholipid conjugate was based upon previous reported syntheses for texaphyrins and phospholipid conjugation protocols involving carbodiimide cross-couplings. Texaphyrins were previously reported through a synthesis that requires a central tripyrrane (3) intermediate, which is formed from 1 through benzyl deprotection and subsequent formylation. Synthetic protocols differ in the preparation from 1 to 3. The main strategy was to develop a texaphyrin with a carboxylate group stemming from the phenyl moiety. From this central intermediate, a variety of phospholipids would then be conjugated using a free hydroxyl site on the lipid. This strategy was highly desired, as it allows for a variety of phospholipids to be conjugated to the texaphyrin moiety, offering route to generate a large library of compounds. Secondly, due to the structural similarity of porphyrins to texaphyrins (viewed as 'expanded porphyrins'), we anticipated reactivities of each macrocycle would be relatively similar. Due to previous reports demonstrating carbodiimide-mediate conjugation of phospholipids to porphyrins, this strategy was employed for texaphyrin-phospholipid conjugation.

3,4-diaminobenzoic acid was reacted with tripyrrane 3 to afford an aromatic carboxylate texaphyrin 5. Gadolinium (III) was subsequently centrally coordinated to the texaphyrin macrocycle, whereby attempts were made to couple 6 with a phospholipid of choice, 1-palmitoyl-2-hydroxy-sn-glycero-3-phosphocholine (lyso-PC). Despite modulation of carbodiimide (EDC, DCC, etc.), and reaction conditions (solvent, temperature, pH), conversion into desired texaphyrin-phospholipid conjugate 7 was unsuccessful. In an effort to determine whether the centrally coordinated metal interfered with phospholipid conjugation, conjugations attempts were carried out between free-base texaphyrin 5 and lyso-PC. As previously observed, conversion into target conjugation product was not obtained.

Method 2 Reaction Scheme:

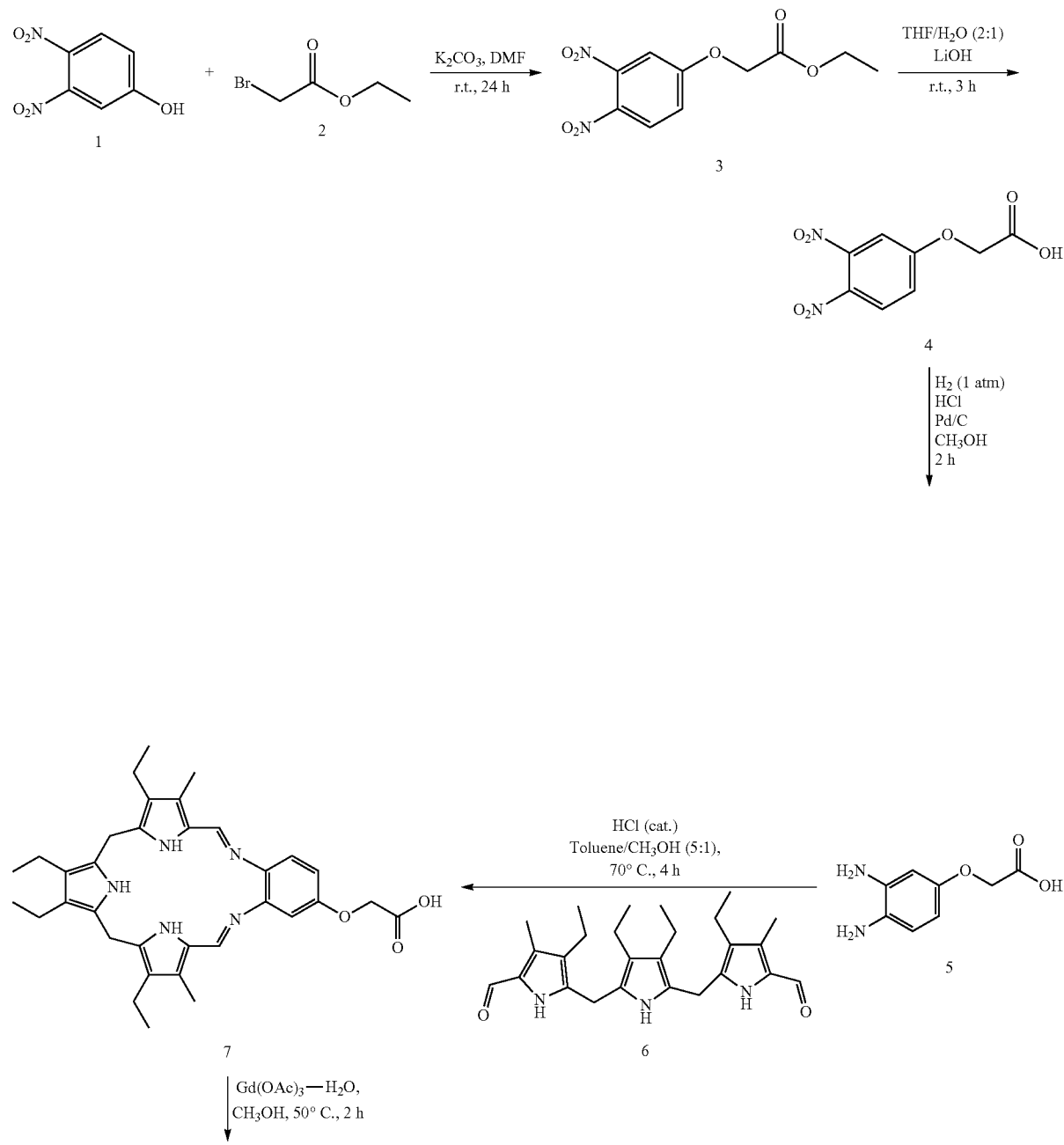

-continued

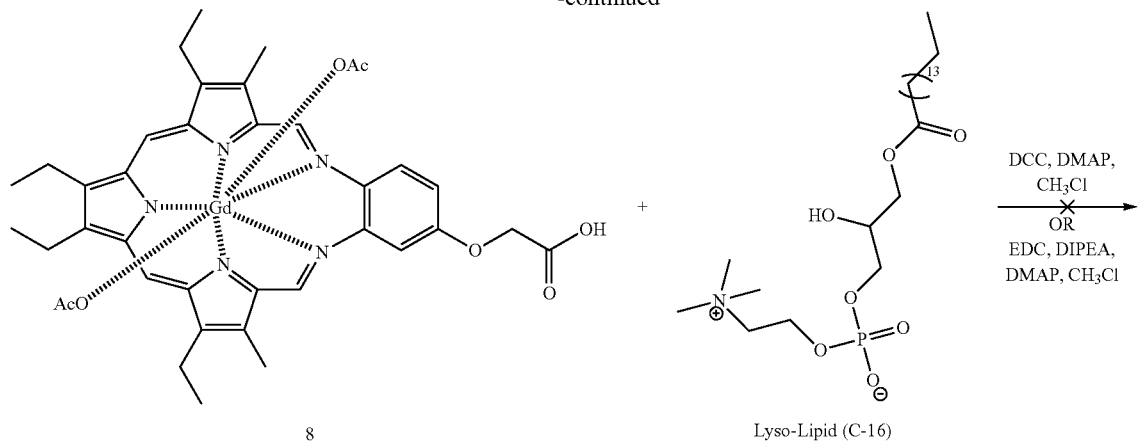

8

Lyso-Lipid (C-16)

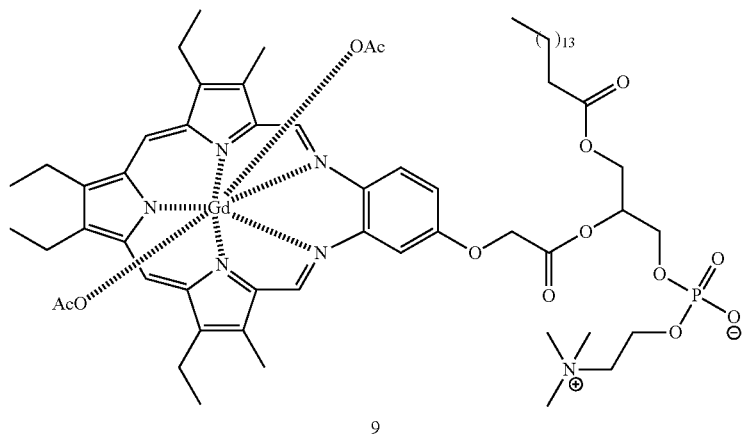

9

Based on these previous findings, it was hypothesized that the aromatic carboxylate could be deactivated and thereby an ineffective coupling partner in carbodiimide-mediate conjugations. To circumvent this, it was hypothesized that an alkyl carboxylate could serve as a more ideal coupling partner for carbodiimide-mediated coupling processes. To test whether this was an effective strategy, a methylene unit was introduced through ether linkage between 3,4-dinitrophenol and ethyl bromoacetate, where by subsequent hydrolysis and reduction afforded 2-(3,4-diaminophenoxy)acetic acid, a candidate alkyl carboxylate derivative. Using previous methods described, an alkyl carboxylate texaphyrin was synthesized, along with its corresponding Gd(III) centrally coordinated counterpart. Attempts were made to conjugate these 'alkyl carboxylate texaphyrins' with phosphocholines, using carbodiimide-mediate coupling.

Despite a variety of conditions and coupling reagents, conjugation of the phospholipid to the alkyl carboxylate texaphyrin was not obtained.

Method 3 Reaction Scheme:

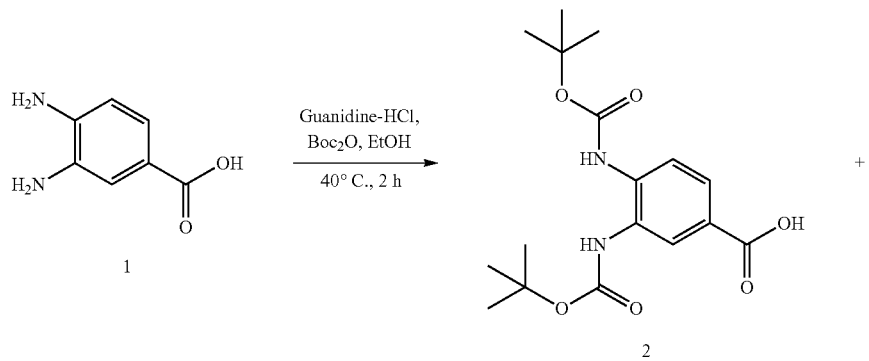

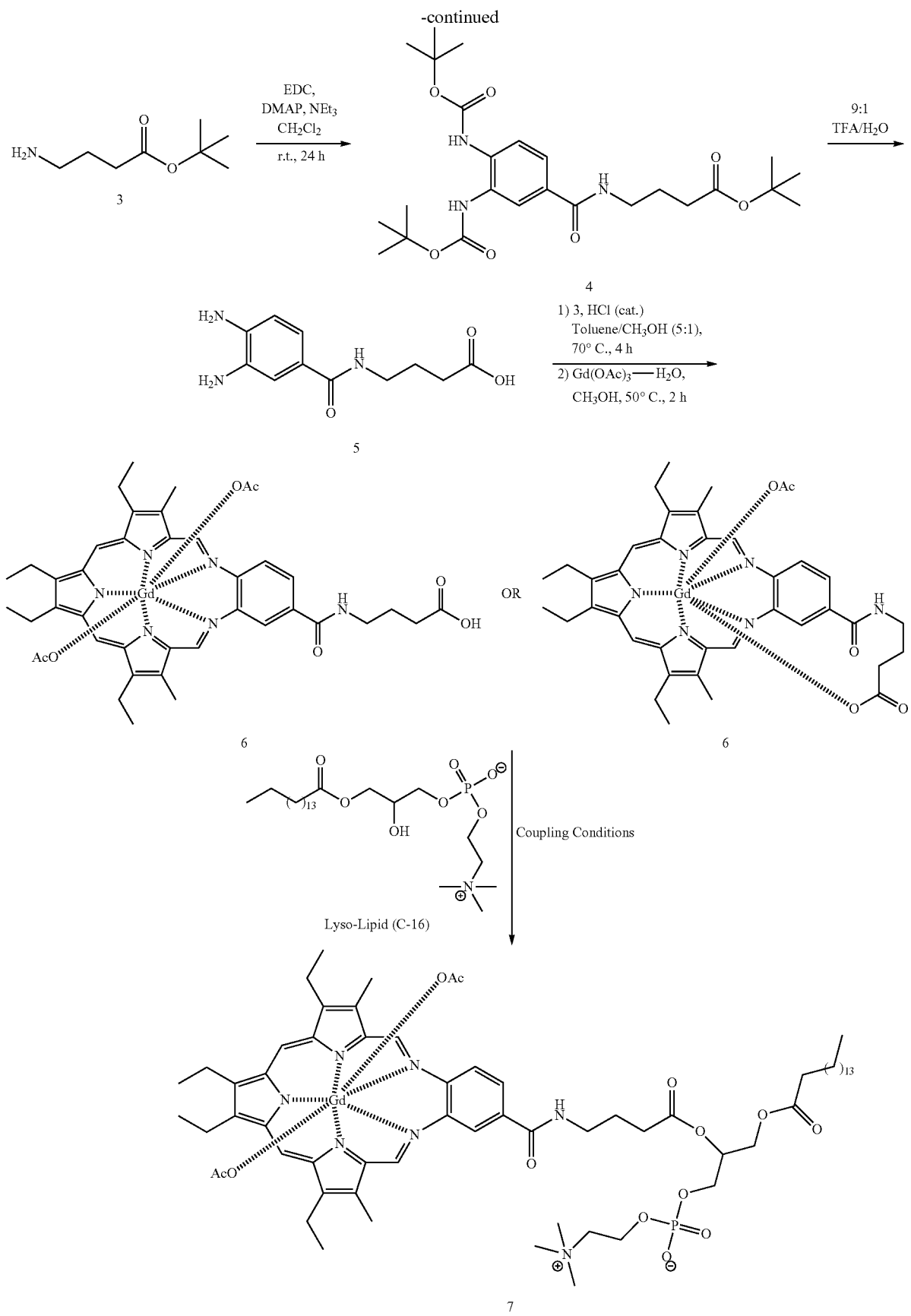

Additional approaches were explored, investigating several substituents and the potential effect on phospholipid conjugation success. A strategy involving the using of an amide branched texaphyrin for phospholipid conjugation was employed. Using 3,4-diaminobenzoic acid, a cost effective reagent, di-boc protection and subsequent peptide conjugation afforded a tri-boc protected intermediate. Triple deprotection in the presence of TFA liberated desired moieties in quantitative yields, whereby reaction with tripyrrane 3 afforded a free base amide-branched carboxylate texaphyrin. Metal (III) coordination was effectively achieved using aforementioned conditions, obtaining coordinated metal (III)-texaphyrin # in excellent yields. Attempts were we made conjugating both free-base texaphyrin and metal (III)-coordinated texaphyrins, using carbodiimide-mediate conjugation with phospholipids. Despite employing a variety of conditions and synthetic protocols, the target texaphyrin-phospholipid conjugate was not obtained in any of the reaction trials. This elucidated the understanding that carboxylate texaphyrins are not suitable substrates in carbodiimide-mediate conjugations with phospholipids, warranting investigations into alternative strategies.

Method 4 Reaction Scheme:

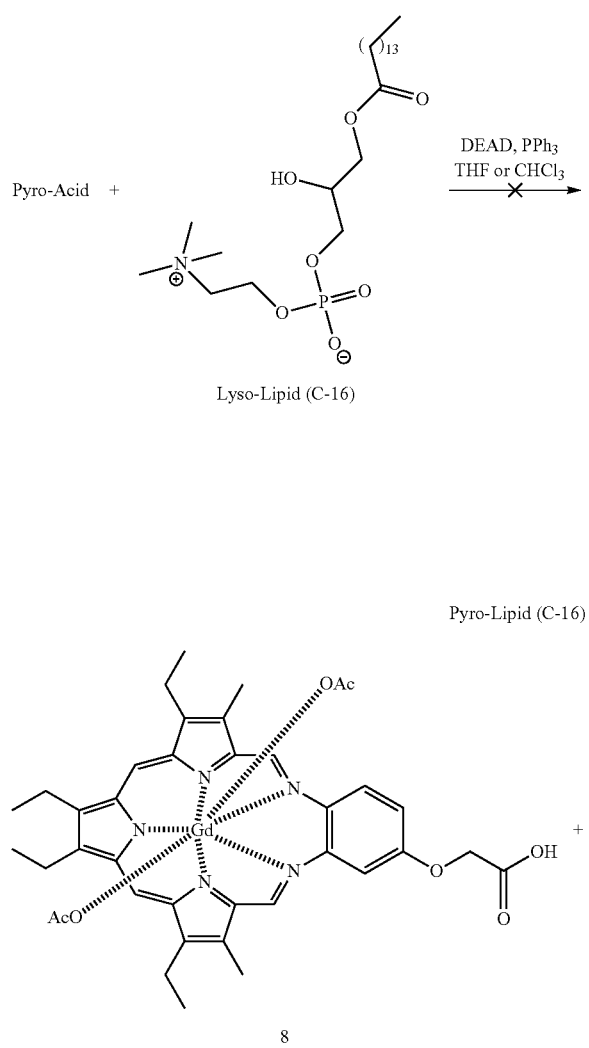

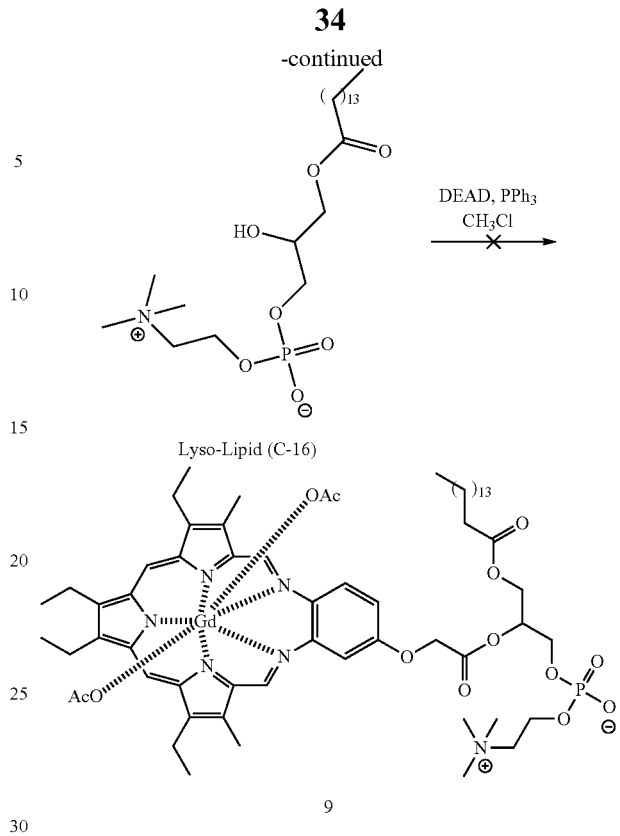

After the failures of carbodiimide-mediated conjugation between carboxylate texaphyrins and phospholipids, alternative strategies were investigated for bond formation between secondary hydroxyls and carboxylates. The Mitsunobu reaction is well known and characterized, displaying a highly effective route in ester formations and inversions of stereochemistry. Given the strong success of this protocol throughout the literature, it was attempted on a carboxylate texaphyrin intermediate, as well as another macrocycle, pyropheophorbide A. The second macrocycle is a porphyrin based one, shares significant similarities with texaphyrins (which are referred to as 'expanded porphyrins'). This second macrocycle was used as a template to determine if porphyrin-based macrocycles behaved similarly with texaphyrin macrocycles, and whether the macrocycle moiety is responsible for the success or failure in the previously attempted conjugation protocols. Numerous synthetic trials were attempted using Mitsunobu conditions on both macrocycle templates, and in every scenario, no conversion to the target phospholipid conjugate was obtained. The led to the discovery that phospholipid conjugations with carboxylate texaphyrins is an ineffective synthetic route, and to circumvent this issue, it is necessary to conjugate the phospholipid onto the diamino building block first, before generating the texaphyrin moiety.

Self-Assembly of Metal-Texaphyrin Lipid Conjugates

Figure 6:
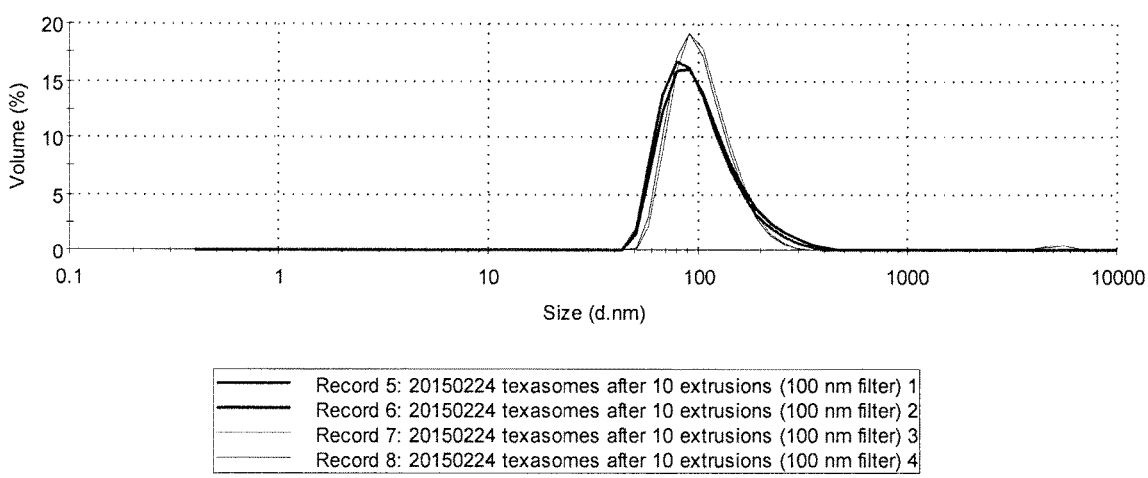
FIG. 6 shows distribution by volume of free-base nano-texaphyrin nanoparticles, obtained through dynamic light scattering. A. DLS size distribution at time zero (immediately after nanoparticle formation). B. DLS size distribution at 48 hours after nanoparticle formation, demonstrating particle stability and integrity.
Figure 6:
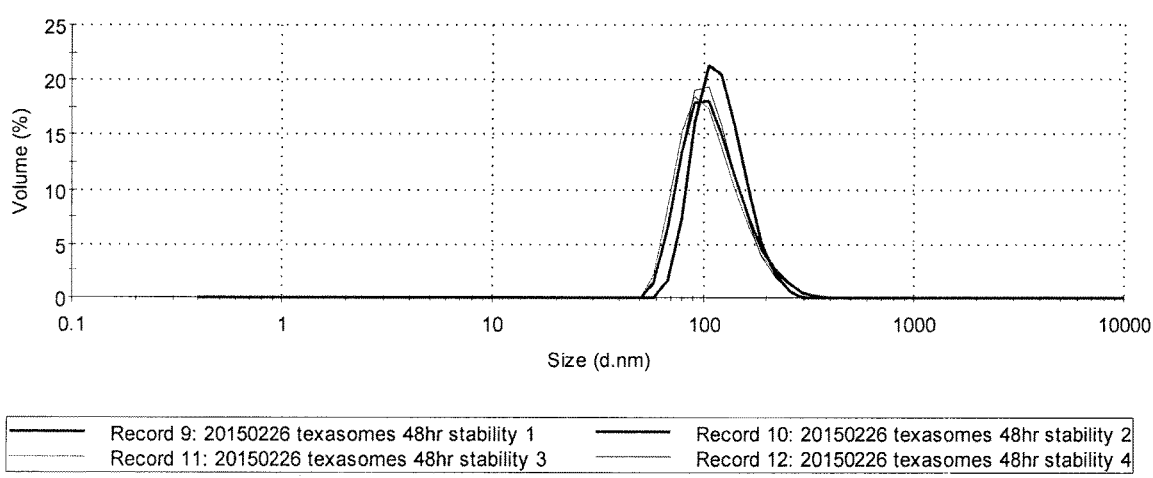

Amphipathic molecules have been demonstrated to undergo self-assembly under certain conditions, attributed to interactions of hydrophobic surfaces with one another, and with hydrophilic moieties to the water front. The structure of texaphyrin-lipid conjugates is in essence an amphipathic, zwitterionic molecule, with a large hydrophilic macrocyclic head, and a long, hydrophobic fatty acid chain. Given the knowledge of self-assembly principles, and applying this to the characteristics of texaphyrin-lipid conjugates, it was predicted that under ideal conditions, free base texaphyrin-lipid and metal-texaphyrin lipid conjugates would undergo self-assembly to form nanostructures of repeating units. It was demonstrated that both the free-base texaphyrin-lipid and metal-texaphyrin lipid conjugates were able to self-assemble readily in suitable conditions, creating nanoparticles with diameters ranging between 100-120 nm, as well as displaying monodispersity (see FIG. 6).

To overcome barriers associated with the administration of free drugs, such as rapid clearance and metabolism and low tumor accumulation, nanoparticles have been used as delivery vehicles. Solid tumors are characterized by irregular and leaky vasculature as well as poor lymphatic drainage, allowing nanoparticles to preferentially be delivered and retained within tumors. In the case of hydrophobic molecules, loading of these drugs has been significantly limited due to the restriction of the drug to the membrane of the vesicle. Porphysome nanovesicles, composed completely of porphyrin-lipid (80 000 porphyrins per 100 nm nanoparticle), have overcome the limited loading capacity of traditional delivery vehicles.[5] The dense packing of porphyrins within each nanoparticle resulted in unprecedented photonic properties with applications in photoacoustic imaging, photothermal therapy and activatable fluorescence imaging (FIG. 1); thereby introducing the first all-organic nanoparticles with intrinsic multimodal photonic properties. In addition, metal ions such as radioactive copper-64 or paramagnetic manganese could be directly incorporated into these building blocks to unlock their potential applications in positron emission tomography (PET) and magnetic resonance imaging (MRI). Based upon the foundation of porphysomes and the structural similarities between porphyrins and texaphyrins, the self-assembly of free base and metal texaphyrin-phospholipid conjugates into Nanotexaphyrin (with greater than 80000 texaphyrin-phospholipids per nanoparticle) will significantly enhance the activity, for both imaging purposes and therapeutic applications. The construct of nanotexaphyrin overcome several current obstacles by: 1) delivering a high payload of texaphyrin in each nanoparticle, 2) prolonging the in vivo circulation time and 3) increasing overall tumor accumulation.

Figure 7:
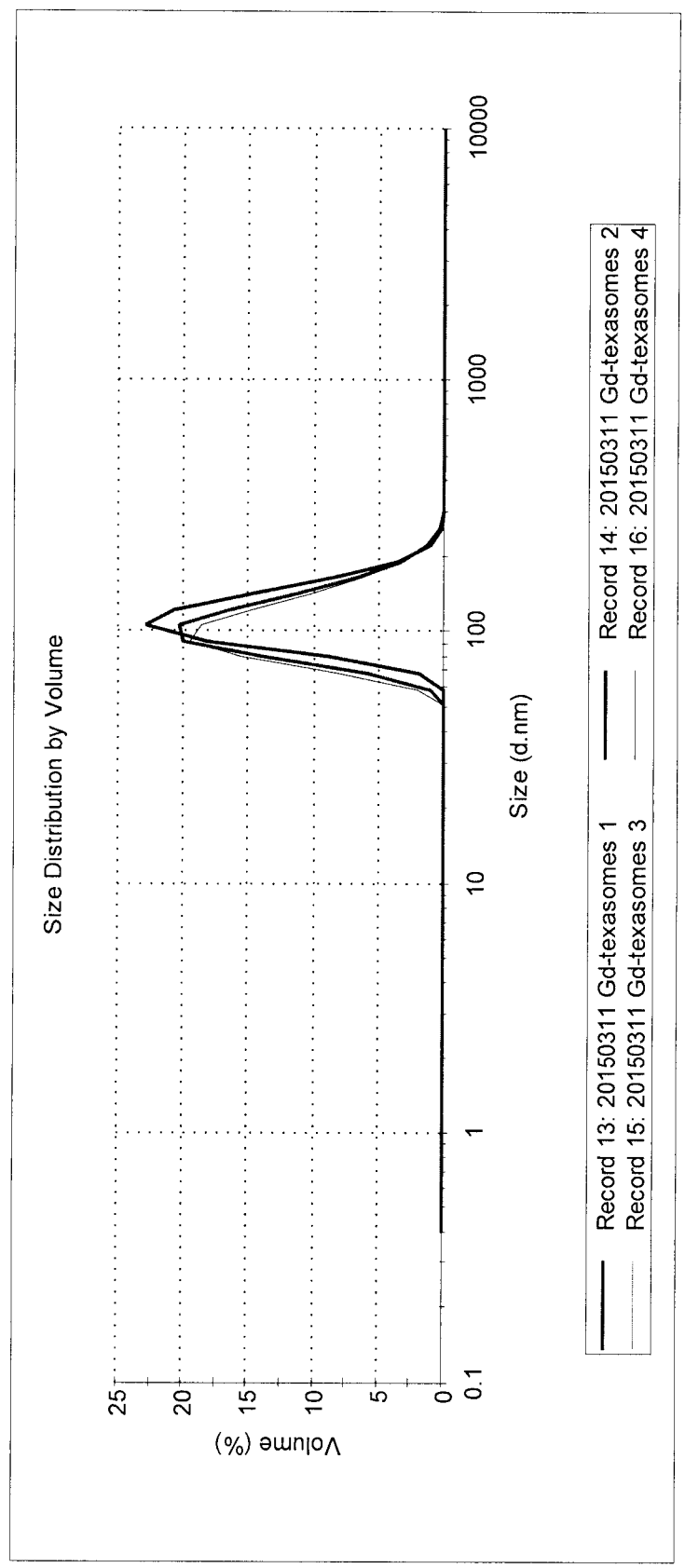
FIG. 7 shows size distribution by volume of Gadolinium-nanotexaphyrin nanoparticles, obtained through dynamic light scattering.
Figure 28:
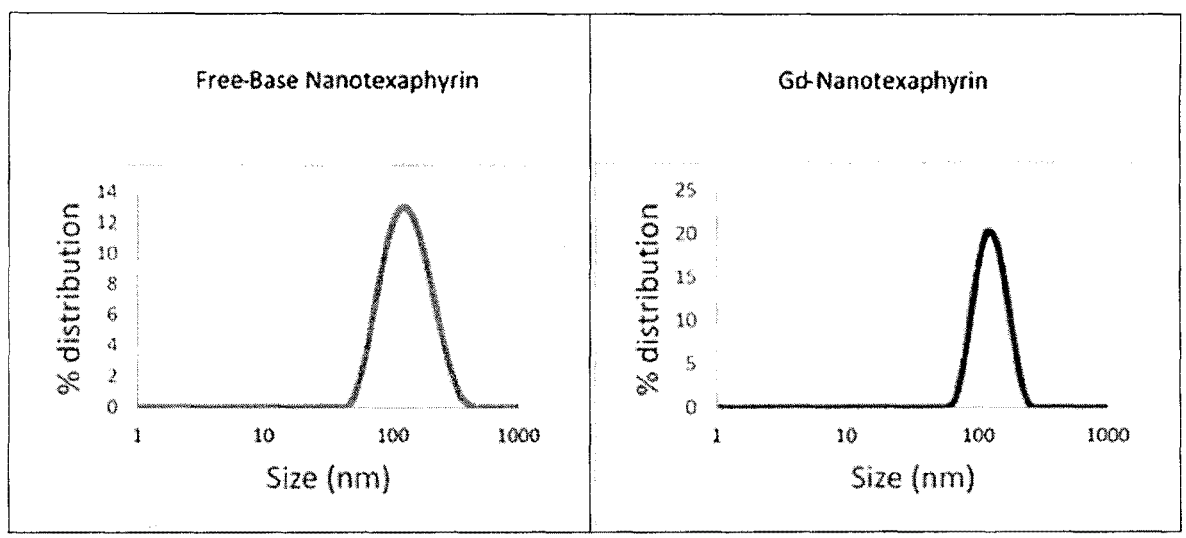
FIG. 28 shows dynamic light scattering profile free-base and Gd-nanotexaphyrins, recorded in PBS.

An example scenario would be a gadolinium-texaphyrin phospholipid nanotexaphyrin. See FIG. 7 for size distribution of gadolinium-nanotexaphyrin nanoparticles and FIG. 28 for dynamic light scattering profiles. Physical characteristics of gadolinium-nanotexaphyrin nanoparticles are listed in Table 1 below.

TABLE 1

Physical characteristics of Gadolinium-nanotexaphyrin nanoparticles

| Characteristic | Dimension (nm) |
| --- | --- |
| Size by Volume | 112.6 ± 3.63 |
| Z-Average | 122.8 ± 2.00 |
| PDI | 0.058 ± 0.018 |

The intrinsic MR property of Gd-texaphyrin can be used to non-invasively monitor the distribution of Gd-texaphyrin in the tumor and in vivo clearance. We anticipate that both a greater radiation enhancement and MRI contrast enhancement will be demonstrated over free Gd-texaphyrin, providing the avenue for Gd-texaphyrin to enter into clinical practice for many different cancer types. Furthermore, the development of nanotexaphyrin will open a plethora of clinical imaging and therapy opportunities. The 5-coordination of texaphyrin building blocks in the nanotexaphyrin will allow stable chelating of a wide array of medical radioisotopes (e.g., $^{90}Y$, $^{111}In$, $^{153}Sm$, $^{166}Ho$, $^{177}Lu$, $^{213}Bi$, etc.), thus launching this nanotechnology into a full spectrum of nuclear medicine applications (SPECT, PET imaging, brachytherapy and alpha therapy, etc.).

MRI Capabilities of MN-Nanotexaphyrin

Figure 8:
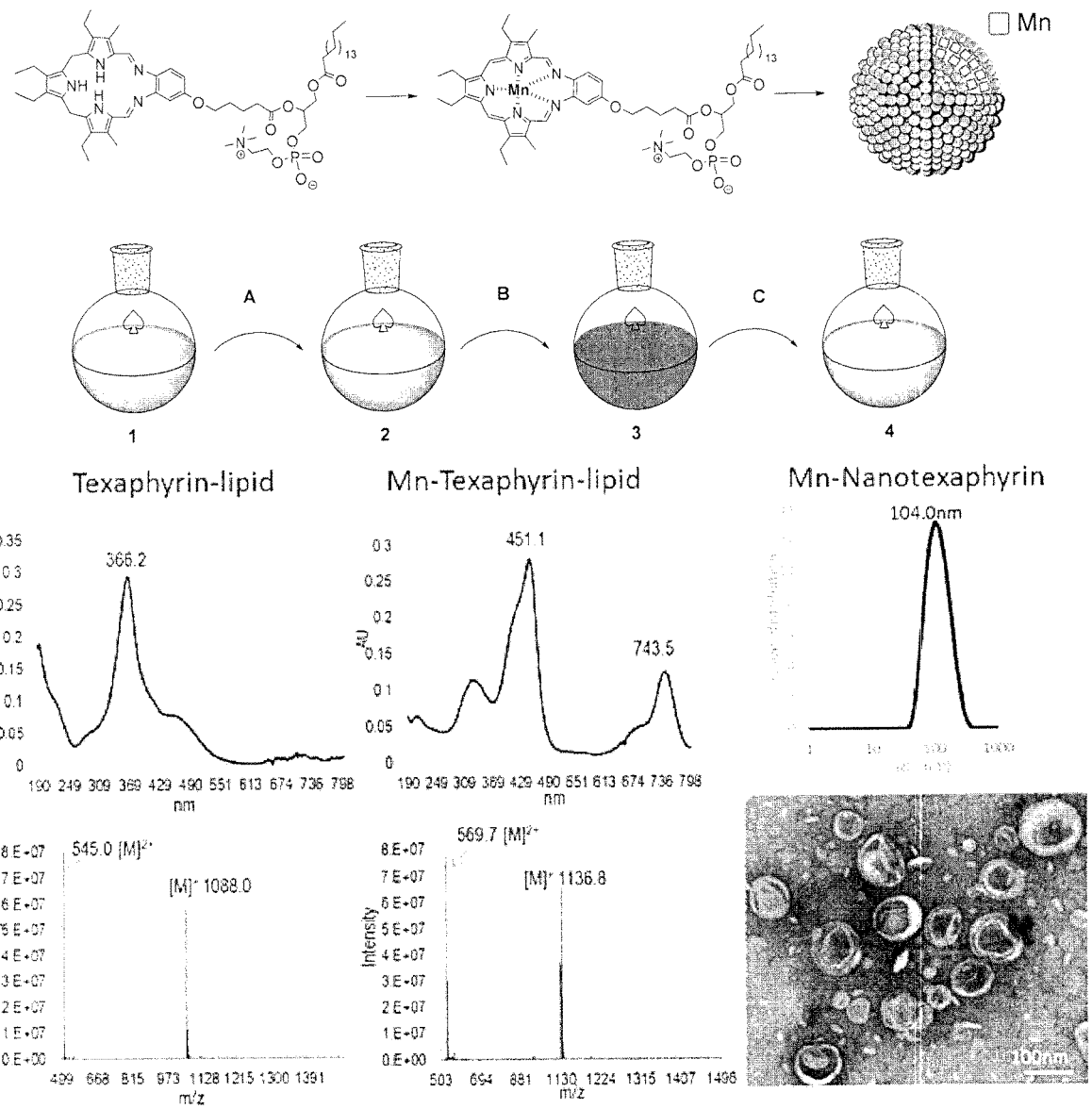
FIG. 8 shows one-pot formation of Mn-nanotexaphyrin.

One-pot formation of Mn-nanotexaphyrin (see FIG. 8): To a reaction vessel is added free-base texaphyrin-phospholipid conjugate (60 mg, 55.18 µmol and $Mn(OAc)_2.(H_2O)_4$ (13.52 mg, 55.18 µmol) in 10 mL of anhydrous MeOH, and is cooled to 0° C. Next, triethylamine (76.71 µL, 551.75 µmol) is added, whereby the instantaneous chelation of Mn is observed by an instant colour change of light red to deep green. Cholesterol (14.83 mg, 40 mol %) and 1,2-distearoyl-sn-glycero-3-phosphoethanolamine-N-[amino(polyethylene glycol)-2000] (DSPE-2KPEG, 13.46 mg, 5 mol %) are introduced, and the solvent is removed under high vacuum, resulting in the formation of a film. Films were rehydrated with PBS (30 mL), subjected to freeze-thaw cycles (8), and extruded with a 100 nm polycarbonate membrane at 75° C. Mn-nanotexaphyrin size was characterized with a Nanosizer ZS90 (Malvern Instruments). TEM images were collected using an FEI Technai 20 microscope with 200 kV accelerating voltage (and 150000× magnification). Samples were deposited on carbon coated copper grids and incubated with 2% uranyl acetate stain to introduce image contrast. Fluorescence quenching of Mn-nanotexaphyrin was characterized using a Fluoromax fluorometer (Horiba Jobin Yvon). Mn-nanotexaphyrin solutions in PBS (intact particles) and PBS with 0.5% Triton-X100 (nanostructure disrupted samples) respectively, were excited at 460 nm and fluorescence emission spectra collected from 600 to 800 nm. The area under the emission peak was integrated and values from intact and dissociated nanoparticles compared.

Example 1

The nanoassembly of a metallo-texaphyrin library started with the synthesis of a manganese (Mn)-texaphyrin-phospholipid building block. The paramagnetic Mn is a potent magnetic resonance imaging (MRI) contrast agent that causes strong reduction of both T1 and T2 relaxation time constants of tissue. Many chelation strategies have been developed to improve Mn delivery on: (i) in vivo stability; (ii) safety; and (iii) contrast enhancement. Porphyrins have been used as a promising chelating macrocycle for Mn,[10] providing fairly stable complexes in vivo, while possessing efficacious contrast enhancement, mostly in the context of $T_1$.[11] Texaphyrin's larger architecture and stronger coordination (5-coordination state) in comparison to traditional porphyrins (4-coordination state) could lead to more stable Mn-based chelation with new properties, such as improvement of stability and relaxivity.

Example 2

Figure 9:
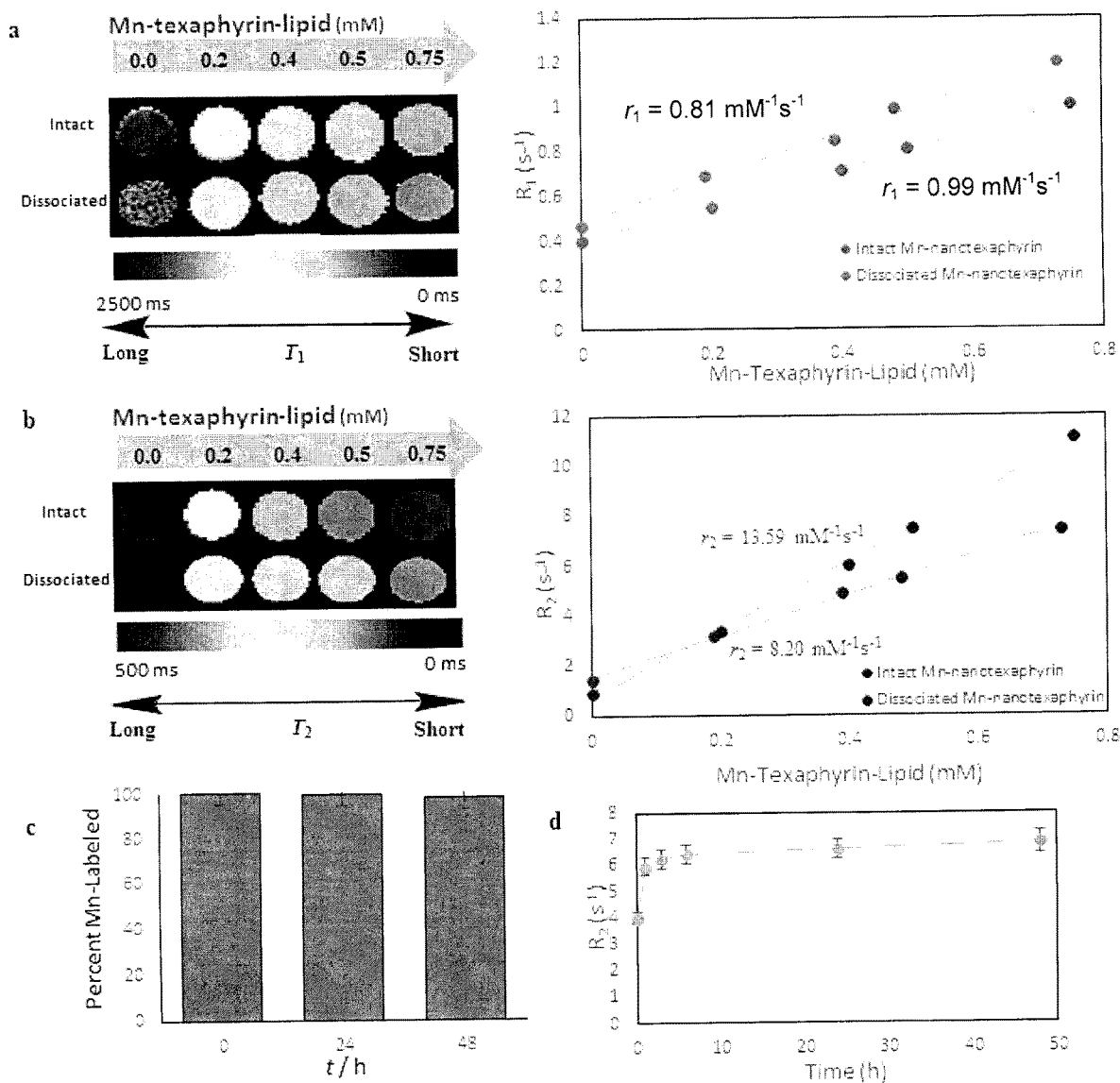
FIG. 9 shows solution-based MRI evaluation at high field strength (7 T) for both T1 and T2 relaxation. Quantitative a) T1 and b) T2 maps of Mn-nanotexaphyrin at varying concentrations in solution with corresponding plots of measured R1 (1/T1) and R2 (1/T2) values along with fitted linear regression lines and relaxivity values, respectively. c) Manganese chelation stability in serum (50% FBS) for 24 and 48 h (n=5). d) Serum stability based on T2 relaxation times.

Mn-nanotexaphyrin was evaluated at a field strength of 7 T. The longitudinal ($r_1$) and transverse ($r_2$) relaxivities were determined by plotting the inverse relaxation time against the Mn-texaphyrin-phospholipid concentration (FIG. 9). Intact Mn-nanotexaphyrins showed a dose-dependent increase in both T1 and T2 weighted images, where marked increases in positive (T1) and negative (T2) contrast enhancement were observed. A calculated $r_1$ of 0.81 $mM^{-1}$ $s^{-1}$ was determined for intact Mn-nanotexaphyrins (FIG. 9a). Geometric calculations for vesicles of 100 nm in diameter composed of phosphatidylcholine headgroups indicate that there are roughly 8×10⁴ texaphyrin conjugates per nanotexaphyrin. Since each texaphyrin in our Mn-nanotexaphyrin composes of a stable 1:1 chelation, this equates to each Mn-nanotexaphyrin carrying approximately 8×10⁴ Mn(II) ions ($r_1$ of 6.48×10⁴ mM⁻¹ s⁻¹ per nanoparticle). After dissociating the Mn-nanotexaphyrins into individual monomers in PBS containing 0.5% Triton X-100, a calculated $r_1$ of 0.99 mM⁻¹ s⁻¹ was established, indicating a 22% enhancement in comparison to the self-assembled construct. The high loading of Mn(II) into each individual nanoparticle, coupled to enhanced delivery and selectivity to neoplastic tissues by the enhanced permeability and retention effect,[12] could offer advantages that are unattainable through the use of individual monomers.

The transverse relaxivity properties of Mn-nanotexaphyrins were also evaluated and compared to corresponding dissociated individual monomers. Intact Mn-nanotexaphyrins demonstrated an $r_2$ of 13.59 mM⁻¹ s⁻¹ at 7 T. Following the same geometric calculations as previously mentioned, each Mn-nanotexaphyrin of 100 nm in diameter possesses an $r_2$ of 1.09×10⁶ mM⁻¹ s⁻¹. Dissociating Mn-nanotexaphyrins to individual monomers lead to a calculated $r_2$ of 8.20 mM⁻¹ s⁻¹, a 60% decrease from intact Mn-nanotexaphyrins. This follows previous reports that increasing particle size leads to increases in $r_2$.[13] The effect is presumably caused by an increase in the relative saturation magnetization with increasing particle size, a correlation demonstrated in ferrites and iron based nanoparticles.[14]

Mn-nanotexaphyrins were able to maintain stable chelation to Mn in the presence of fetal bovine serum (FBS). The stability was evaluated by uPLC-MS which allows clear distinction between free-base texaphyrin-phospholipid and Mn-texaphyrin-phospholipid by the absorption spectra and mass spectrometry. The stability of Mn-chelation to nanotexaphyrin was 99.5±0.8% and 98.8±0.8% after 24 and 48 h in 50% FBS, respectively, thus demonstrating the strong affinity of Mn to the texaphyrin macrocycle chelator (FIG. 9c). Since Mn-coordination causes the "sp³-texaphyrin" to become fully aromatic when chelating a metal ion, the thermodynamic favourability of aromaticity might contribute to the strong affinity of texaphyrin to Mn, and resilience to Mn dissociation. The structural stability of Mn-nanotexaphyrin in serum was evaluated by T2-weighted imaging, where structural degradation can be observed due to a drop in $R_2$ values, as previously mentioned. 0020

Mn-nanotexaphyrin in 50% FBS was shown to possess structural stability for up to 48 h, with no significant decrease in $R_2$ (FIG. 9d). Instead, a slight initial increase in $R_2$ was observed in the presence of FBS (compared to the sample in PBS), indicating Mn-nanotexaphyrin particles might form a protein corona, increasing in the relative saturation magnetization with a larger particle size.

0.5% Triton X-100, a calculated $r_1$ of 0.99 mM⁻¹ s⁻¹ was established, indicating a 22% enhancement in comparison to the self-assembled construct. The high loading of Mn(II) into each individual nanoparticle, coupled to enhanced delivery and selectivity to neoplastic tissues by the enhanced permeability and retention effect,[8] could offer advantages that are unattainable through the use of individual monomers.

The transverse relaxivity properties of Mn-nanotexaphyrins were also evaluated and compared to corresponding dissociated individual monomers. Intact Mn-nanotexaphyrins demonstrated an $r_2$ of 13.59 mM⁻¹ s⁻¹ at 7 T. Following the same geometric calculations as previously mentioned, each Mn-nanotexaphyrin of 100 nm in diameter possesses an $r_2$ of 1.09×10⁶ mM⁻¹ s⁻¹. Dissociating Mn-nanotexaphyrins to individual monomers lead to a calculated $r_2$ of 8.20 mM⁻¹ s⁻¹, a 60% decrease from intact Mn-nanotexaphyrins. This follows previous reports that increasing particle size leads to increases in $r_2$.[9] The effect is presumably caused by an increase in the relative saturation magnetization with increasing particle size, a correlation demonstrated in ferrites and iron based nanoparticles.[10]

Mn-nanotexaphyrins were able to maintain stable chelation to Mn in the presence of fetal bovine serum (FBS). The stability was evaluated by uPLC-MS which allows clear distinction between free-base texaphyrin-phospholipid and Mn-texaphyrin-phospholipid by absorption and mass spectra. The stability of Mn-chelation to nanotexaphyrin was 99.5±0.8% and 98.8±0.8% after 24 and 48 h in 50% FBS, respectively, thus demonstrating the strong affinity of Mn to the texaphyrin macrocycle chelator (FIG. 9c). Since Mn-coordination causes the "sp³-texaphyrin" to become fully aromatic when chelating a metal ion, the thermodynamic favourability of aromaticity might contribute to the strong affinity of texaphyrin to Mn, and resilience to Mn dissociation. The structural stability of Mn-nanotexaphyrin in serum was evaluated by T2-weighted imaging, where structural degradation can be observed due to a drop in $R_2$ values, as previously mentioned.

Mn-nanotexaphyrin in 50% FBS was shown to possess structural stability for up to 48 h, with no significant decrease in $R_2$ (FIG. 9d). Instead, a slight initial increase in $R_2$ was observed in the presence of FBS (compared to the sample in PBS), indicating Mn-nanotexaphyrin particles might form a protein corona, increasing in the relative saturation magnetization with a larger particle size.

Figure 10:
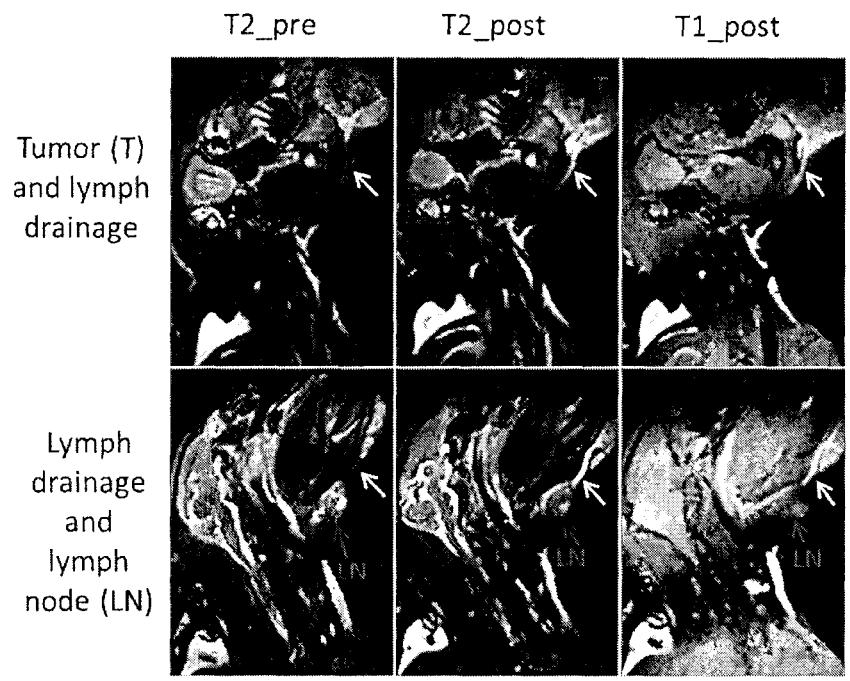
FIG. 10 shows T1- and T2-weighted imaging of the tumour site (top) and lymph node (bottom) of a VX-2 head and neck tumor bearing rabbit. Mn-nanotexaphyrin (8 mg/mL, 1.5 mL), was injected subcutaneously surrounding the tumor area. After 2 h, T1- and T2-weighted imaging was performed on a 7 T preclinical MR imaging system, showing enhanced visualization of lymphatic drainage from the tumor site to adjacent lymph nodes. The represented figure shows sagittal T1- and T2-weighted imaging of the head and neck area, T2 pre-injection, T2 post injection and T1 post injection of the tumor site (top) and the cervical metastatic LN (bottom). Clear signal enhancement was detected after the injection of Mn-nanotexaphyrin demonstrated the lymphatic drainage (yellow arrows).

Mn-nanotexaphyrin was evaluated for the capacity to have contrast enhancement in a lymphoscintigraphy procedure, which relies upon the accumulation of the agent in sentinel lymph nodes (SLNs) using a VX-2 head and neck tumor bearing rabbit with cervical lymph node metastases. Subcutaneous injection of Mn-nanotexaphyrin proximal to the tumor site was evaluated for its capacity to aid in visual enhancement of lymphatic drainage from the tumor site. The 2 h post-injection of Mn-nanotexaphyrin, T1- and T2-weighted imaging showed increased visualization of lymphatic drainage from the tumor site to the adjacent metastatic lymph node (FIG. 10). As a proof-of-concept, the images support the notion that Mn-nanotexaphyrin appears to drain from the injection site towards the lymph node, thereby providing contrast enhancement in this area. Additionally, while still a proof-of-concept, these results highlight the potential utility of Mn-nanotexaphyrin for in vivo imaging as a MRI contrast agent for SLN biopsy procedures.

Figure 11:
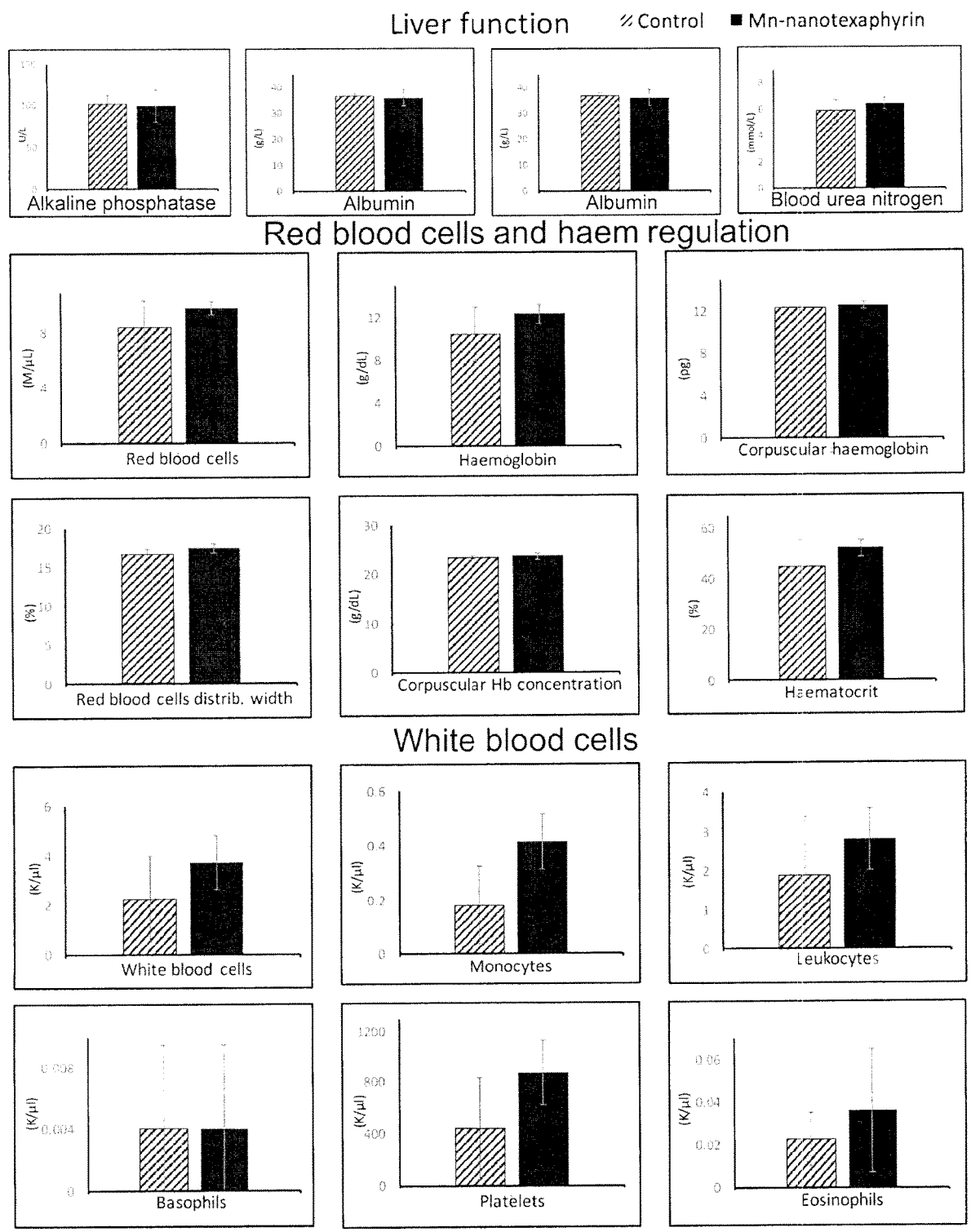
FIG. 11 shows blood test parameters for control mice and after intravenous administration of Mn-nanotexaphyrin (mean±s.d., n=5), p>0.05 for all blood test between Mn-nanotexaphyrin and control groups, indicating non-significant changes induced by Mn-nanotexaphyrin injection.
Figure 12:
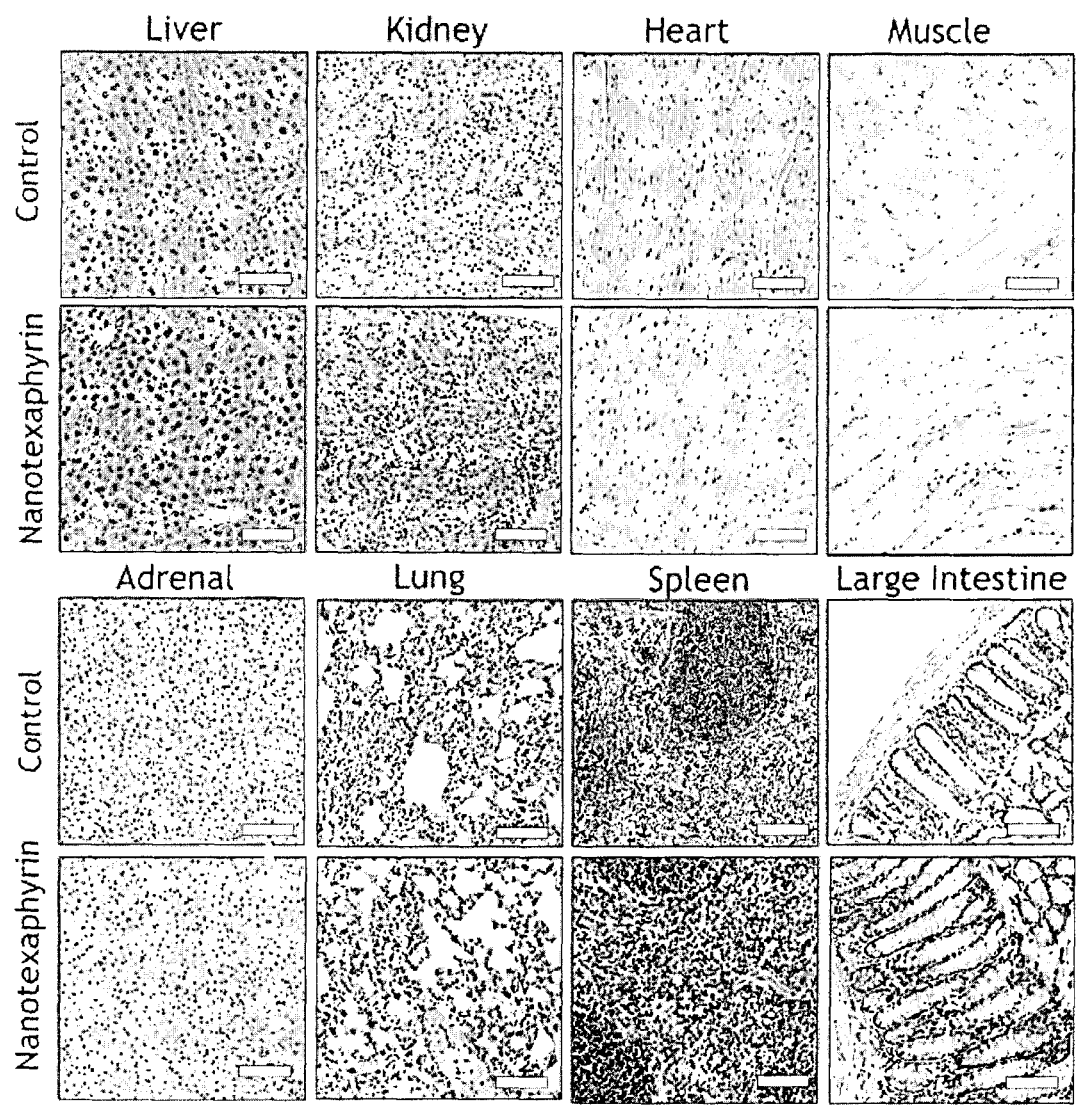
FIG. 12 shows representative haematoxylin and eosin stained sections of indicated organs from mice 24 h after intravenous injection of 10 mg·kg$^{-1}$ Mn-nanotexaphyrin or PBS (control). Scale bar=100 nm.

A toxicity study evaluated the safety of Mn-nanotexaphyrin, investigating potential acute toxicity effects (FIG. 11). Healthy female BALB/c mice (n=5) were injected with high dose (10 mg·kg⁻¹) of Mn-nanotexaphyrin. After 24 h post injection mice were sacrificed and the blood was collected through cardiac puncture. Blood was collected from the control group of mice of the same age and gender, and was used as a reference for the tested parameters. We also demonstrated that treatment with a high dose of Mn-nanotexaphyrin does not affect the level of diagnostically significant liver enzymes. Counts of red blood cells and haem level did not significantly change, demonstrating unaffected physiological regulation of endogenous porphyrins. No change in white blood cells counts indicates that Mn-nanotexaphyrin is non-immunogenic in the acute phase. Major organs from the control and experimental groups of animals were harvested and sent for histopathology analysis (FIG. 12), further demonstrating that Mn-nanotexaphyrin does not exhibit acute toxicity effects at 24 h post injection.

Figure 13:
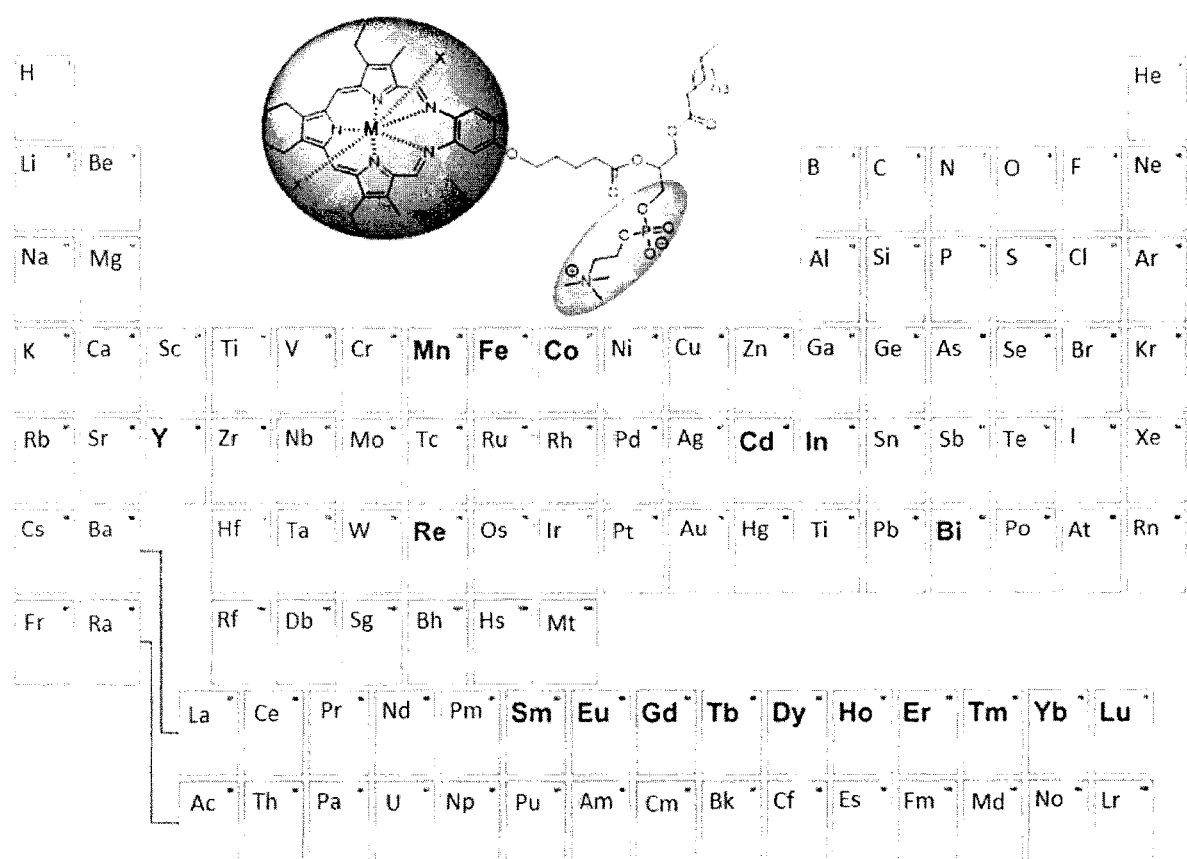
FIG. 13 shows the texaphyrin-phospholipid conjugate chelation library. Elements demonstrated to have stable 1:1 chelation are represented in bold.
Figure 14:
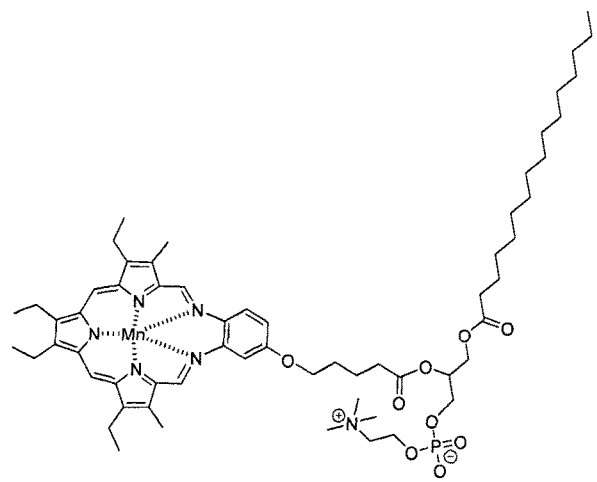
FIG. 14 shows characterizations for Manganese(II)-texaphyrin complex. A. Photodiode array spectrum (range from 200-800 nm). B. High-resolution mass spectrometry, indicating M+Z and corresponding fragmentation pattern.
Figure 14:
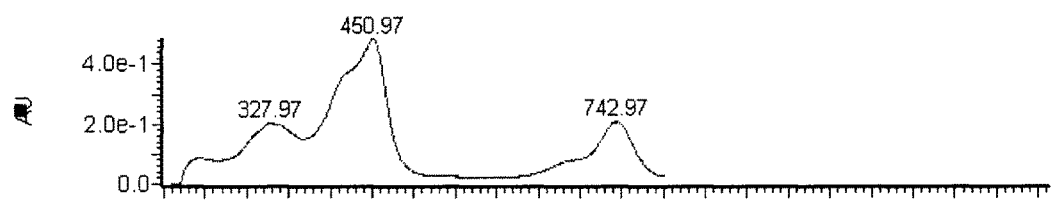
Figure 14:
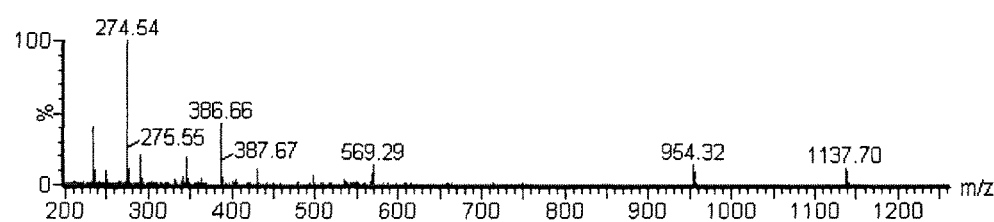
Figure 15:
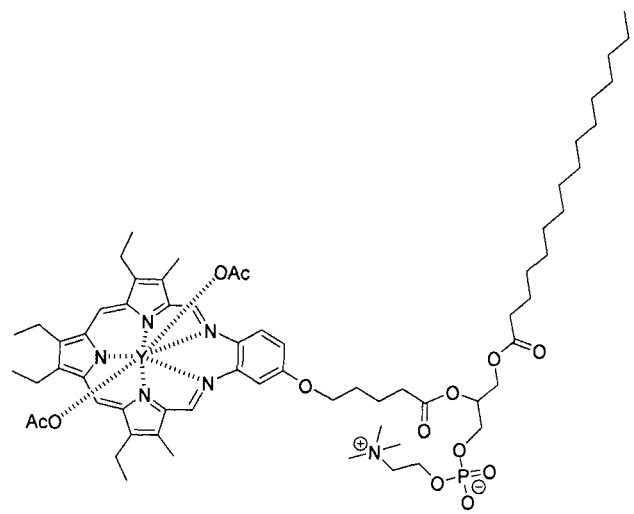
FIG. 15 shows characterizations for Yttrium(III)-texaphyrin complex. A. High-resolution mass spectrometry, indicating M+Z and corresponding fragmentation pattern. B. Photodiode array spectrum (range from 200-800 nm).\
Figure 15:
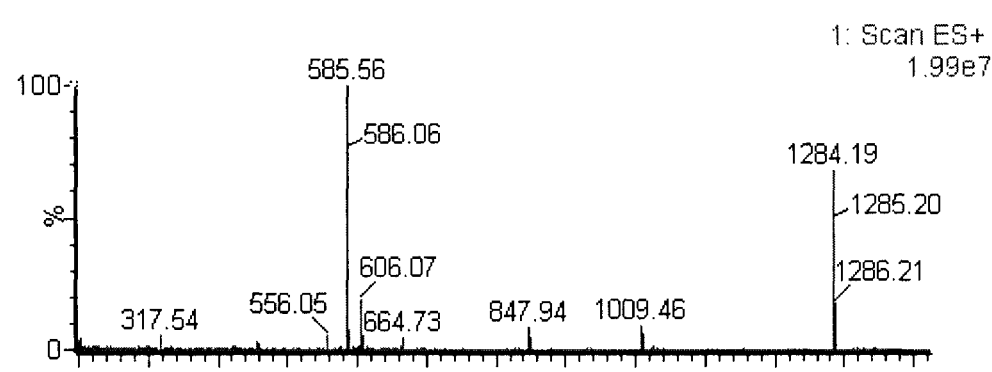
Figure 15:
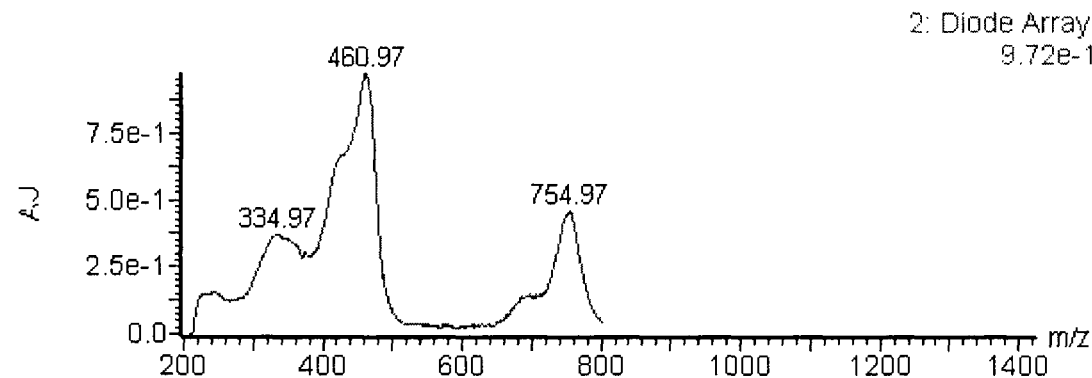
Figure 16:
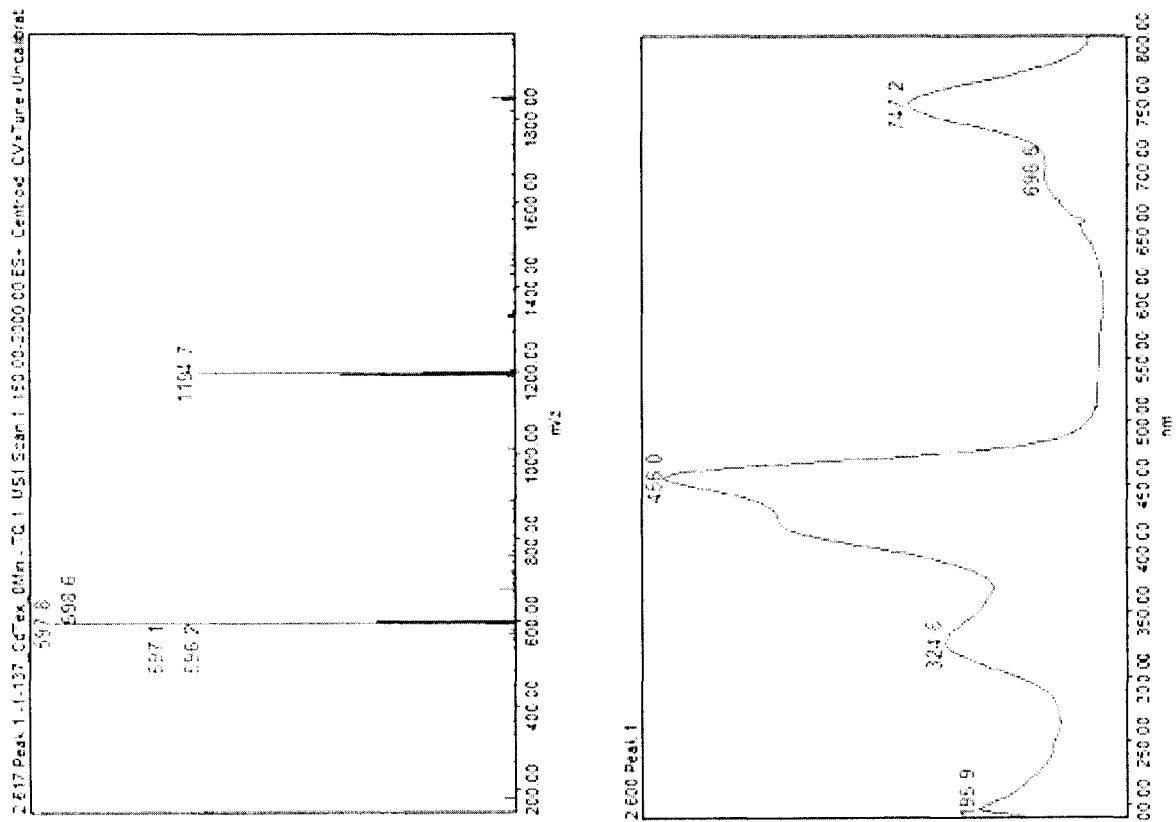
FIG. 16 shows characterizations for Cadmium(III)-texaphyrin complex. A. High-resolution mass spectrometry, indicating M+Z and corresponding fragmentation pattern. B. Photodiode array spectrum (range from 200-800 nm).
Figure 16:
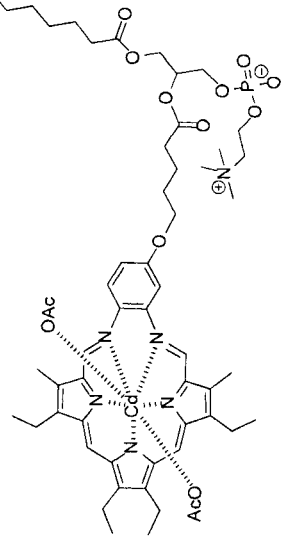
Figure 17:
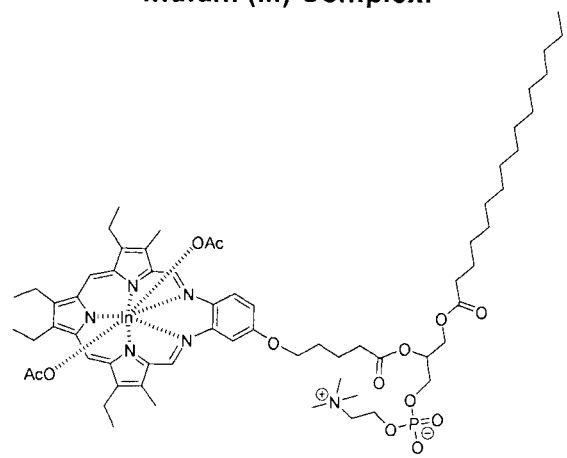
FIG. 17 shows characterizations for Indium(III)-texaphyrin complex. A. High-resolution mass spectrometry, indicating M+Z and corresponding fragmentation pattern. B. Photodiode array spectrum (range from 200-800 nm).
Figure 17:
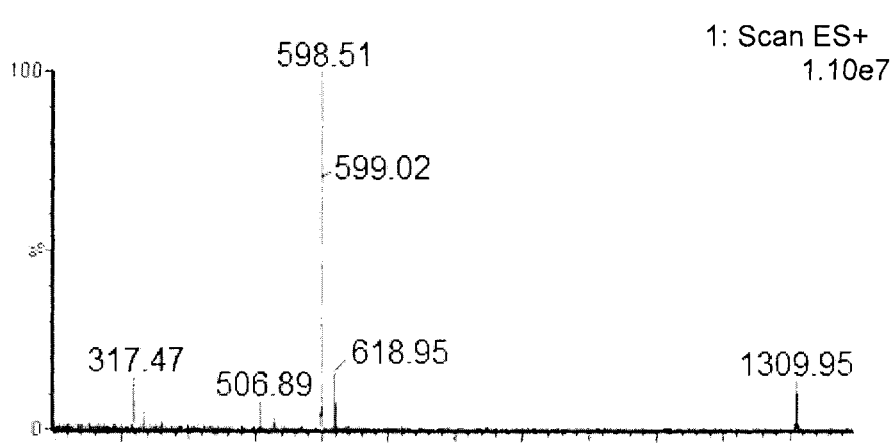
Figure 17:
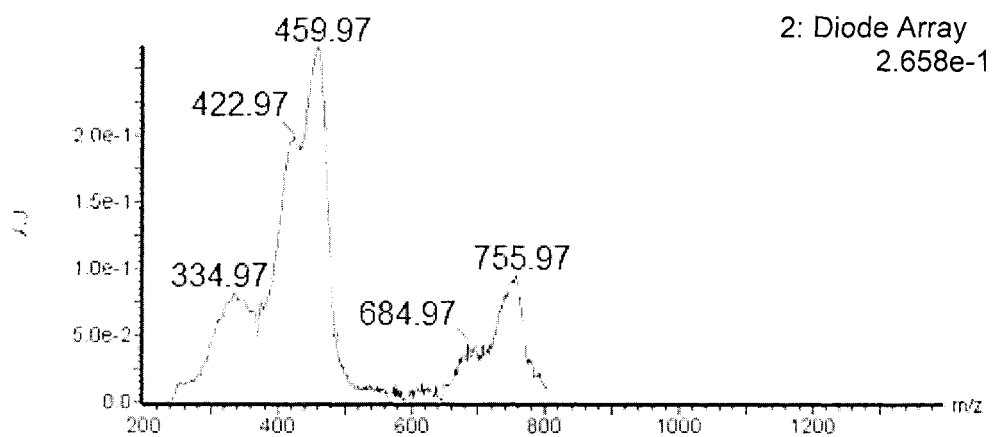
Figure 18:
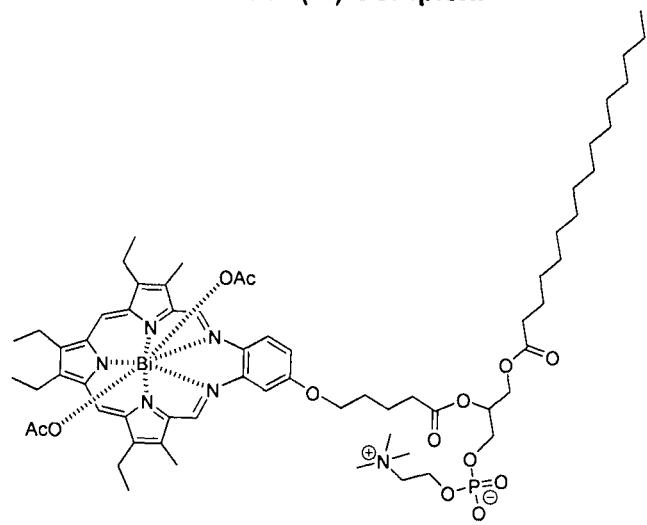
FIG. 18 shows characterizations for Bismuth(III)-texaphyrin complex. A. High-resolution mass spectrometry, indicating M+Z and corresponding fragmentation pattern. B. Photodiode array spectrum (range from 200-800 nm).
Figure 18:
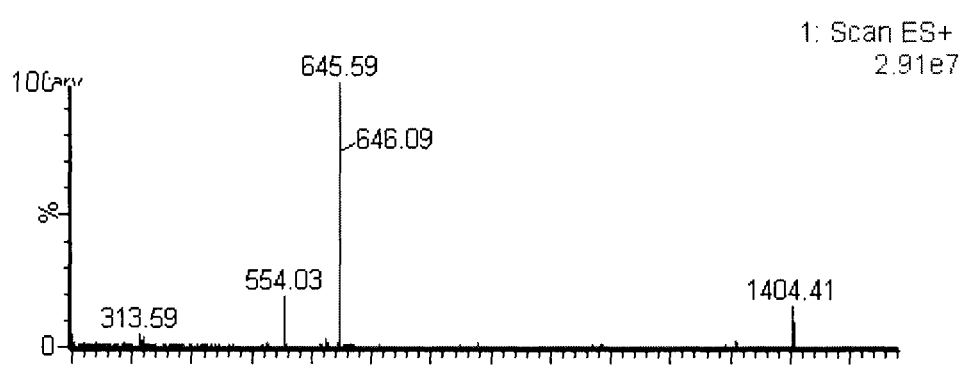
Figure 18:
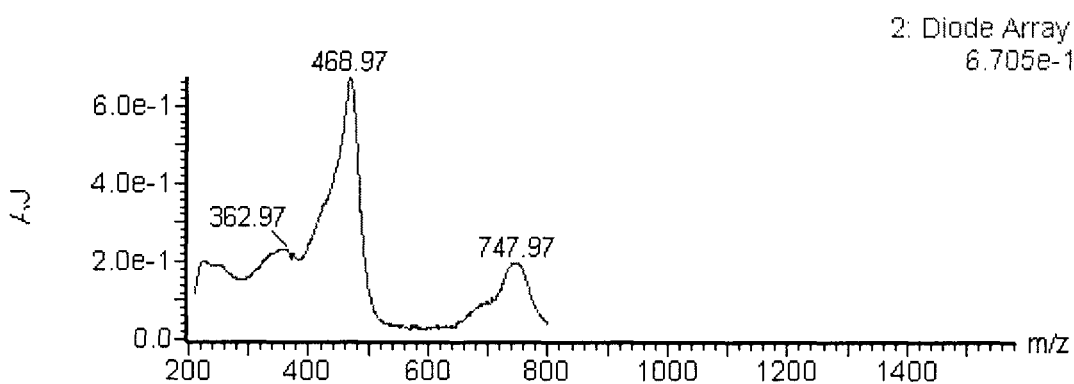
Figure 19:
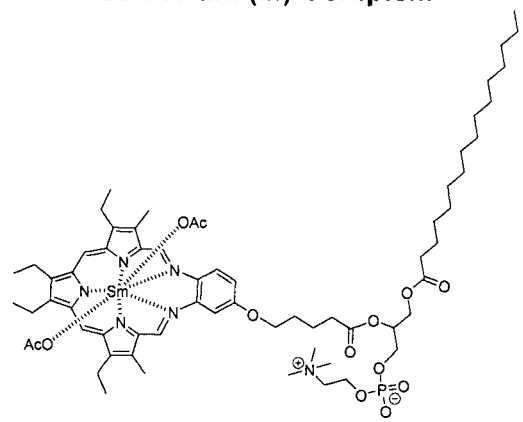
FIG. 19 shows characterizations for Samarium(III)-texaphyrin complex. A. High-resolution mass spectrometry, indicating M+Z and corresponding fragmentation pattern. B. Photodiode array spectrum (range from 200-800 nm).
Figure 19:
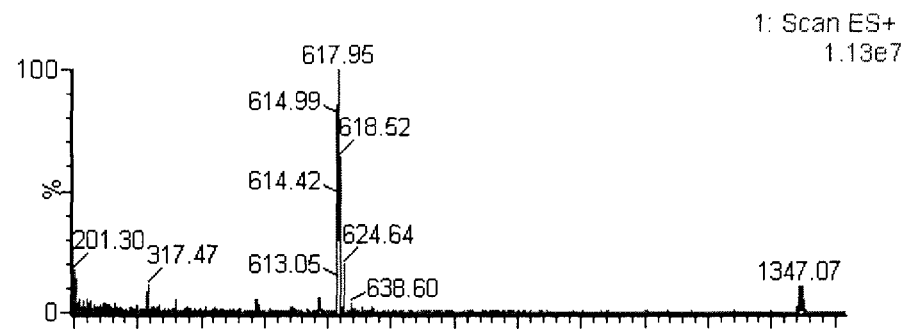
Figure 19:
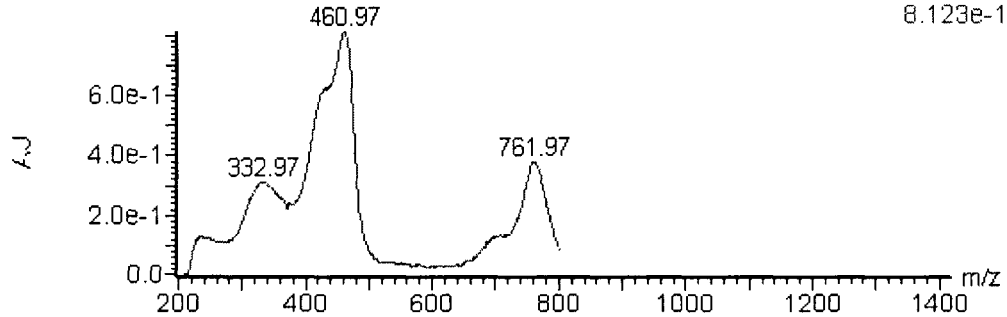
Figure 20:
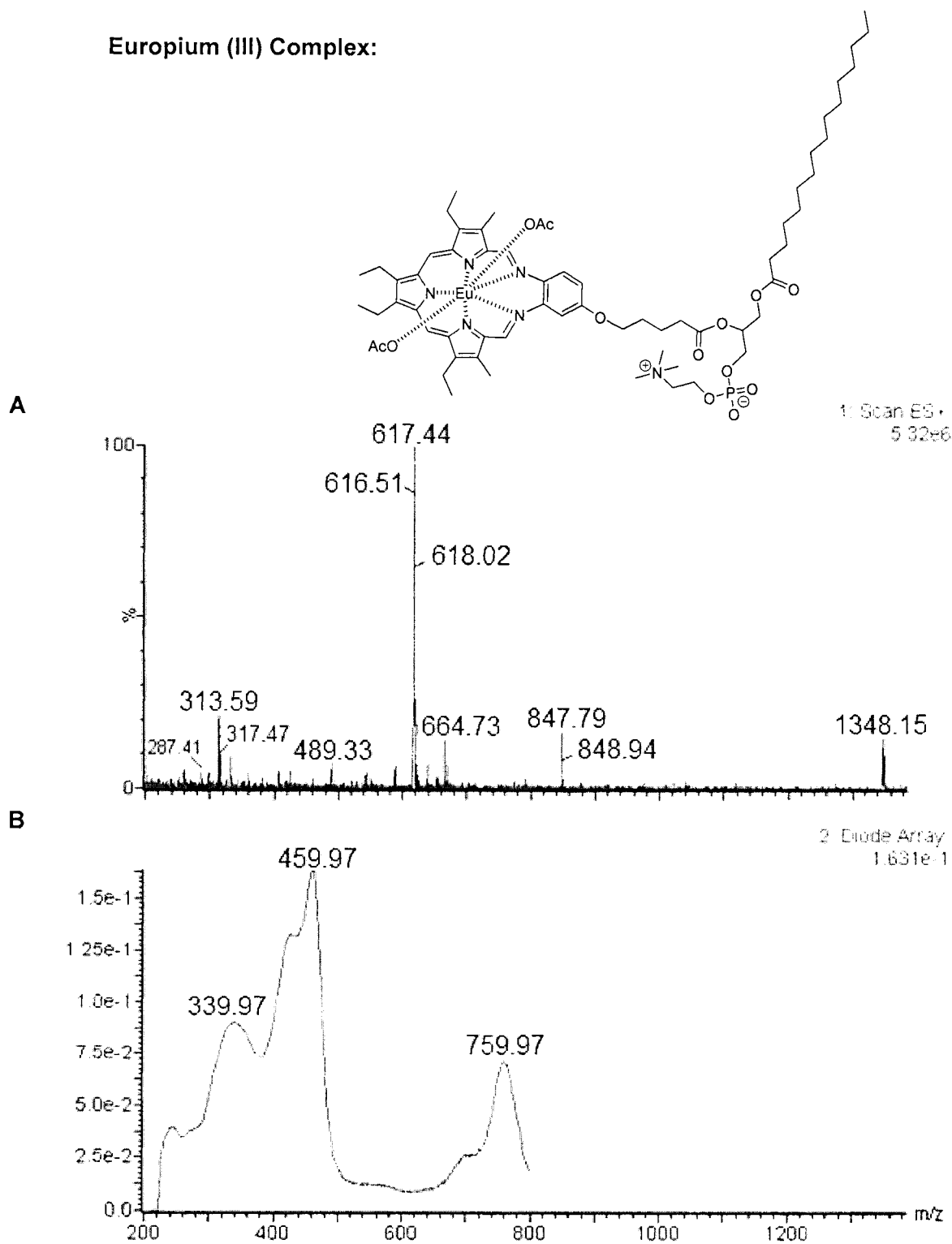
FIG. 20 shows characterizations for Europium(III)-texaphyrin complex. A. High-resolution mass spectrometry, indicating M+Z and corresponding fragmentation pattern. B. Photodiode array spectrum (range from 200-800 nm).
Figure 21:
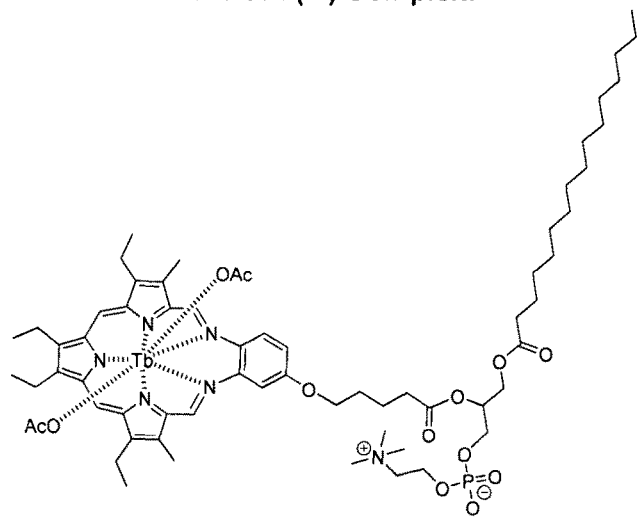
FIG. 21 shows characterizations for Terbium(III)-texaphyrin complex. A. High-resolution mass spectrometry, indicating M+Z and corresponding fragmentation pattern. B. Photodiode array spectrum (range from 200-800 nm).
Figure 21:
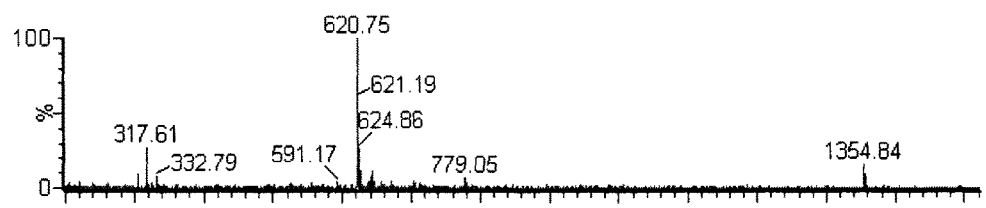
Figure 21:
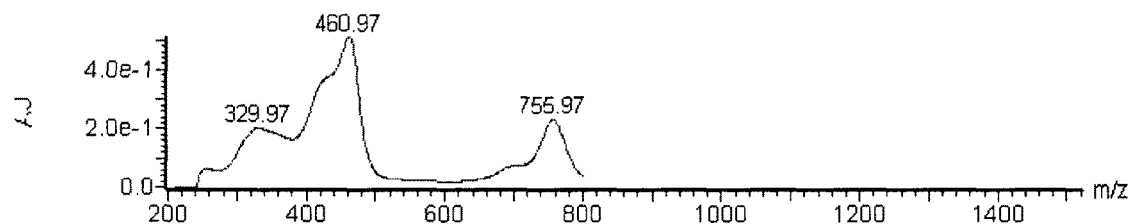
Figure 22:
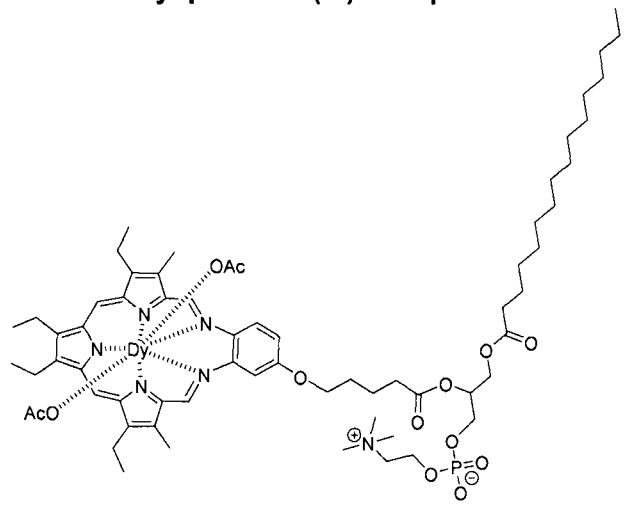
FIG. 22 shows characterizations for Dysprosium(III)-texaphyrin complex. A. High-resolution mass spectrometry, indicating M+Z and corresponding fragmentation pattern. B. Photodiode array spectrum (range from 200-800 nm).
Figure 22:
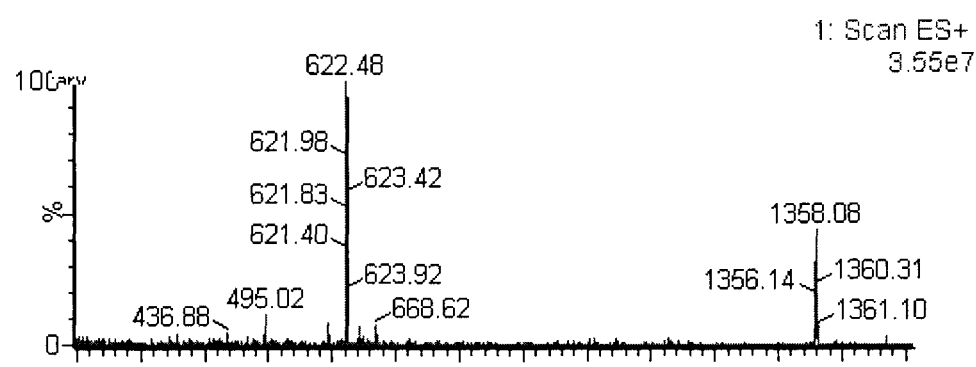
Figure 22:
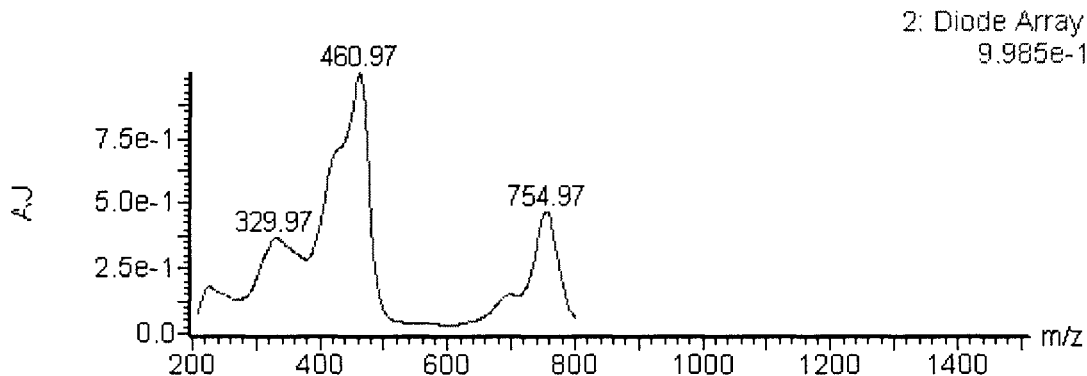
Figure 23:
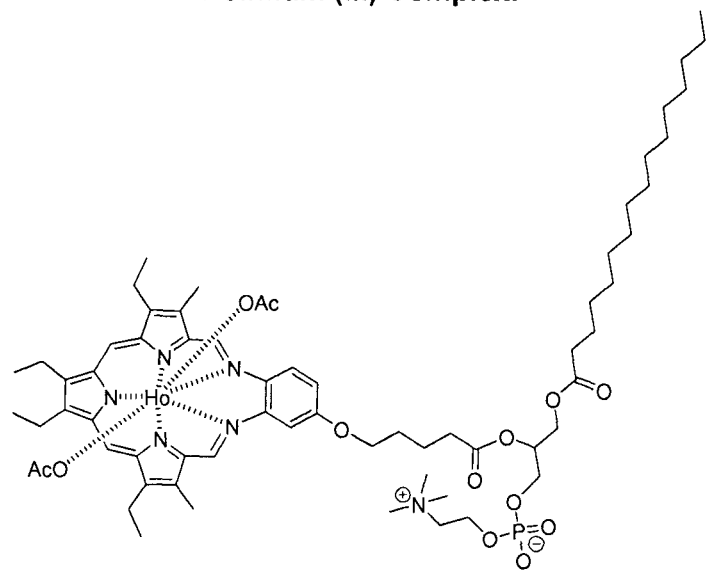
FIG. 23 shows characterizations for Holmium(III)-texaphyrin complex. A. High-resolution mass spectrometry, indicating M+Z and corresponding fragmentation pattern. B. Photodiode array spectrum (range from 200-800 nm).
Figure 23:
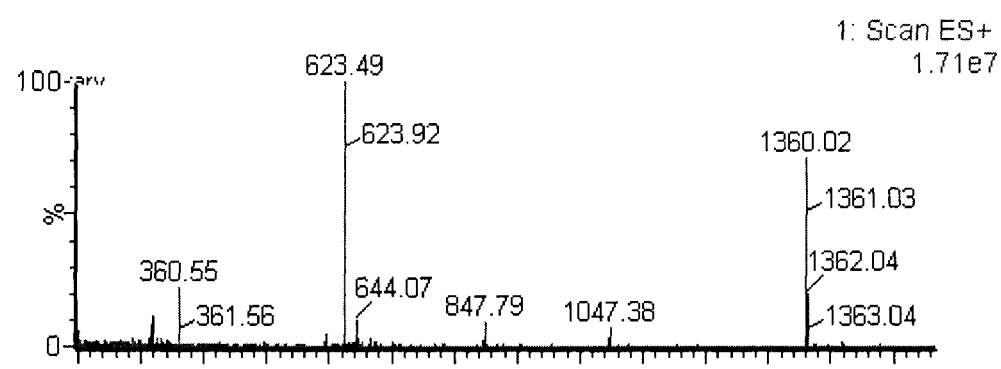
Figure 23:
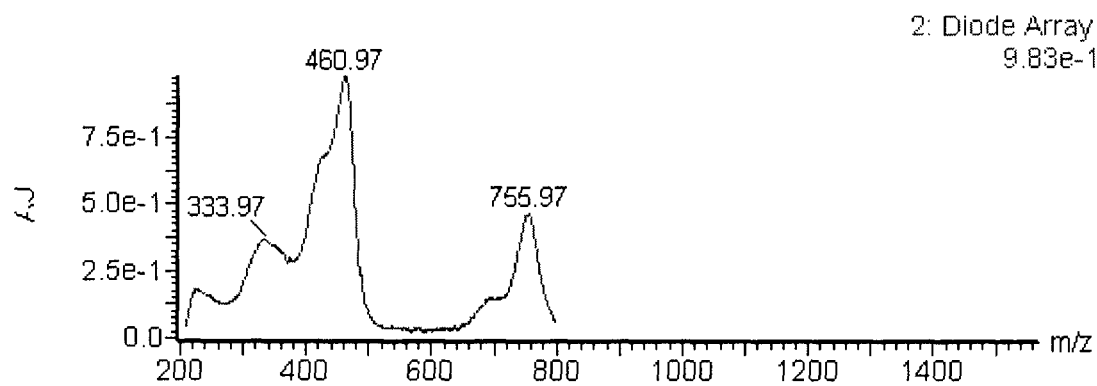
Figure 24:
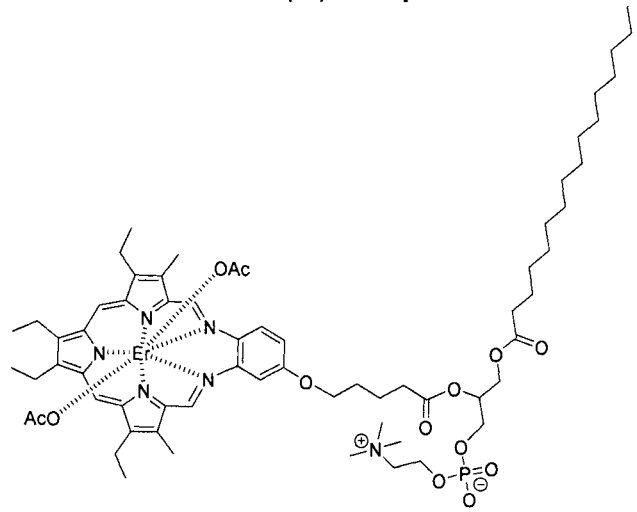
FIG. 24 shows characterizations for Erbium(III)-texaphyrin complex. A. High-resolution mass spectrometry, indicating M+Z and corresponding fragmentation pattern. B. Photodiode array spectrum (range from 200-800 nm).
Figure 24:
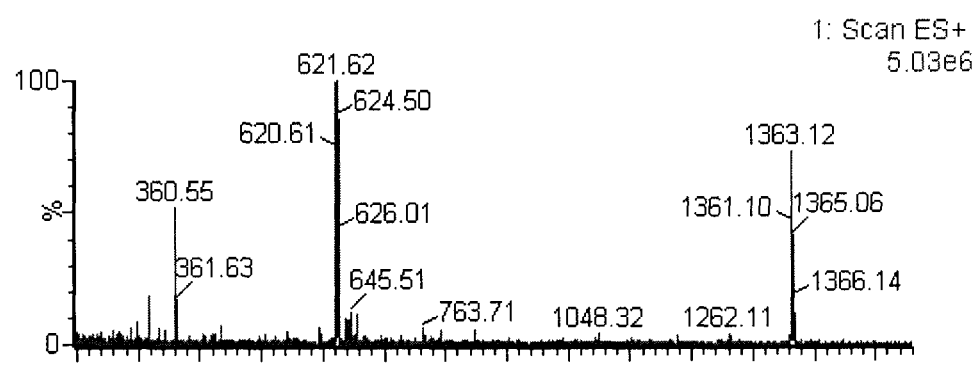
Figure 24:
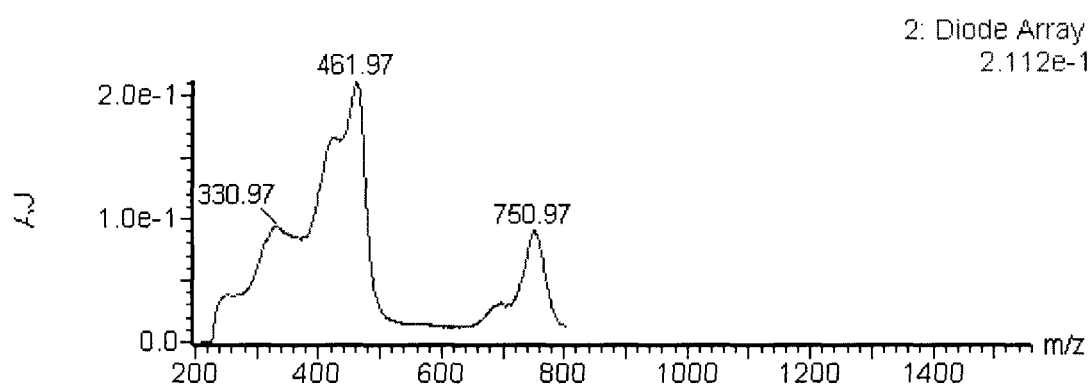
Figure 25:
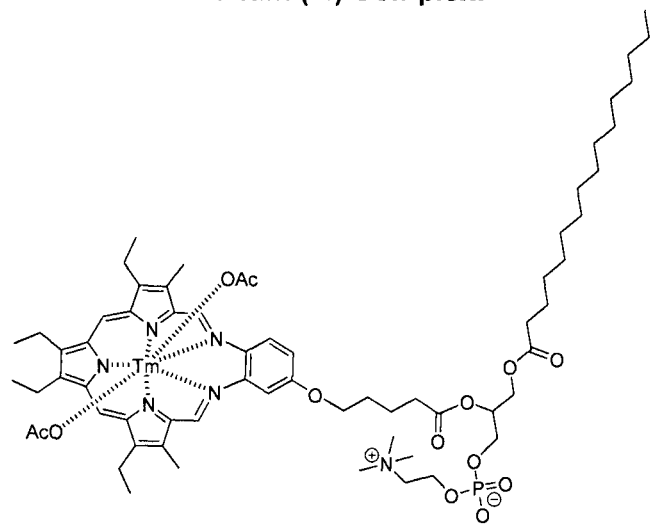
FIG. 25 shows characterizations for Thulium(III)-texaphyrin complex. A. High-resolution mass spectrometry, indicating M+Z and corresponding fragmentation pattern. B. Photodiode array spectrum (range from 200-800 nm).
Figure 25:
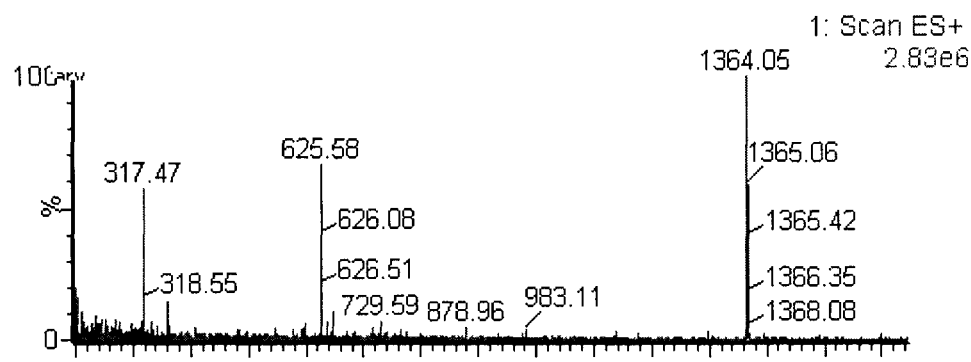
Figure 25:
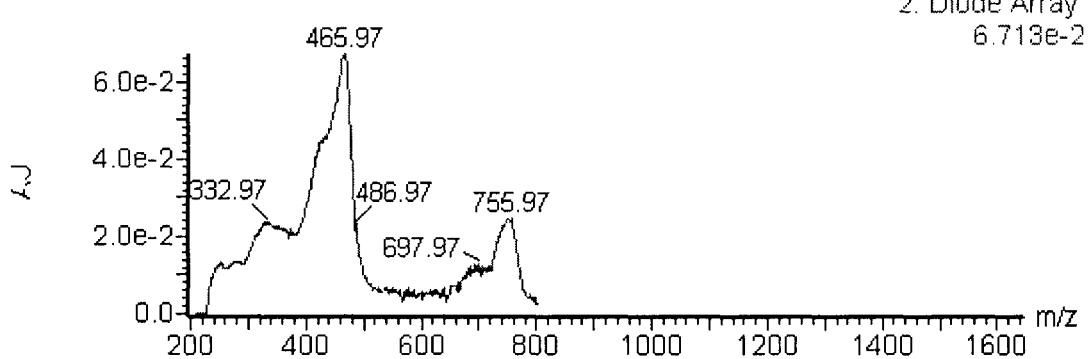
Figure 26:
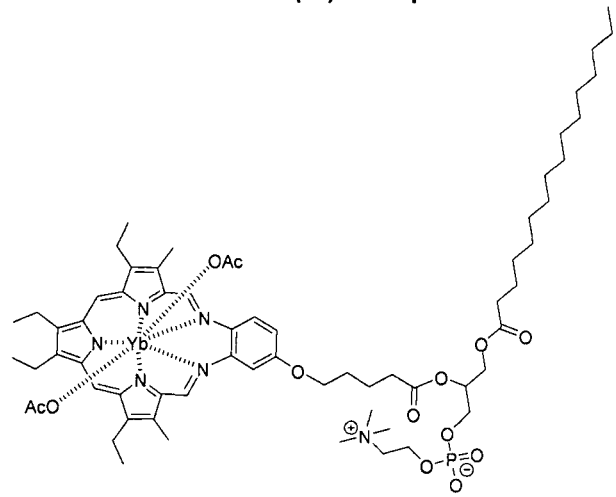
FIG. 26 shows characterizations for Ytterbium(III)-texaphyrin complex. A. High-resolution mass spectrometry, indicating M+Z and corresponding fragmentation pattern. B. Photodiode array spectrum (range from 200-800 nm).
Figure 26:
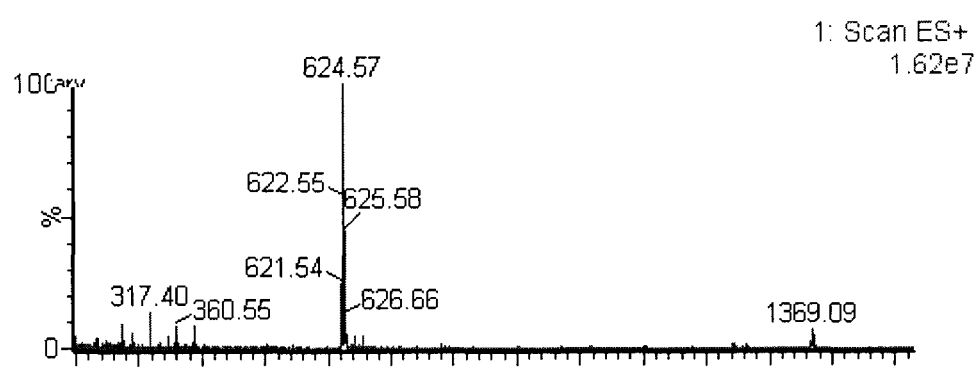
Figure 26:
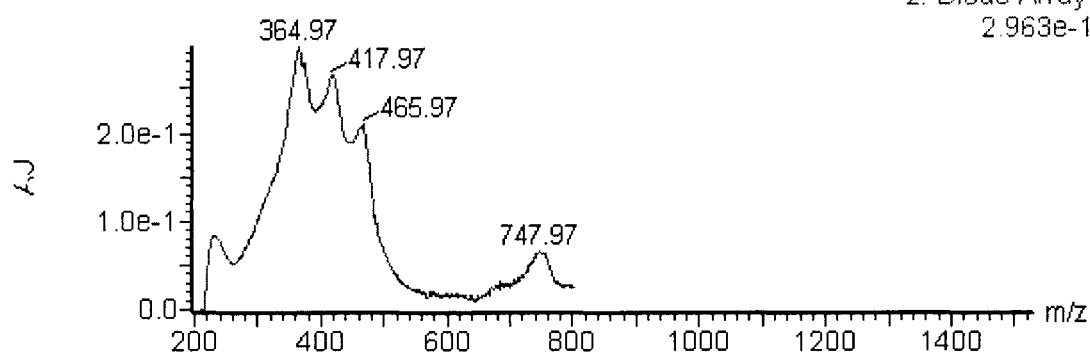
Figure 27:
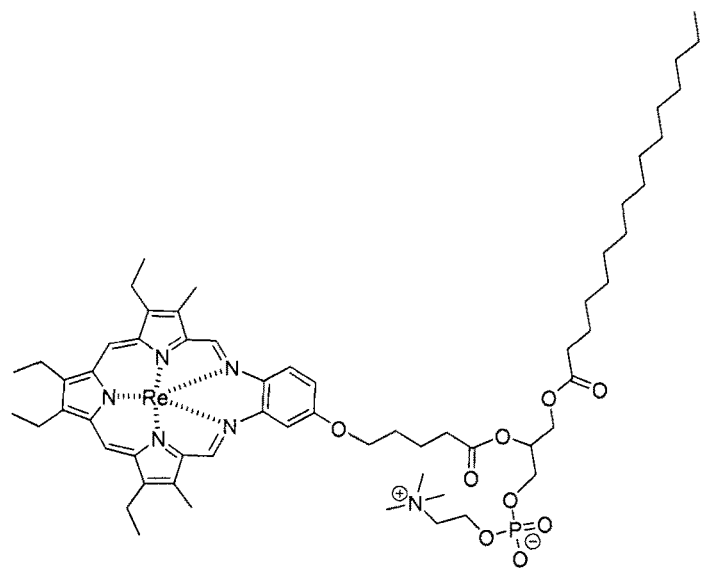
FIG. 27 shows characterizations for Rhenium(II)-texaphyrin complex. A. High-resolution mass spectrometry, indicating M+Z and corresponding fragmentation pattern. B. Photodiode array spectrum (range from 200-800 nm).
Figure 27:
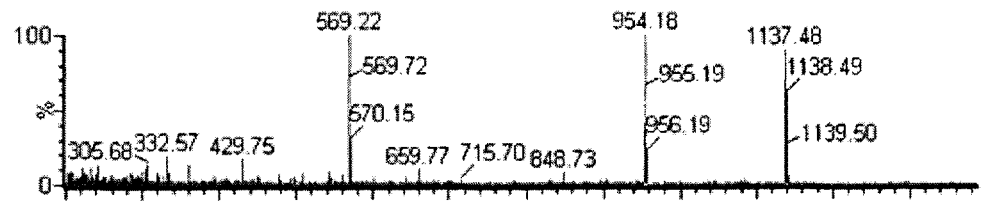
Figure 27:
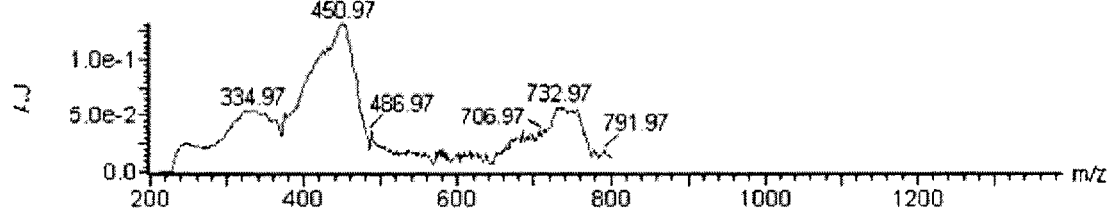

Demonstrating the versatility of metal chelations with texaphyrin-phospholipid conjugate, 17 metallo-texaphyrin-phospholipid conjugates were synthesized (FIG. 13). The diverse library of metallo-texaphyrin-conjugates each have their own unique, intrinsic properties and subsequent applications in radiotherapy, radiosensitization, PET and SPECT imaging, MRI, photodynamic therapy, and fluorescence imaging. Moreover, these metal-texaphyrin-phospholipids can be combined to create mixed nanotexaphyrins with multifunctionality.

MN-Nanotexaphyrin Evaluations

Chelation Stability:

Mn-texaphyrin-phospholipid in PBS were mixed 1:1 with FBS and incubated at 37° C. At 0, 24 and 48 h, small aliquots were used to evaluate the chelation stability. The percentage of Mn-chelation calculated through integration of free-base texaphyrin phospholipid and Mn-texaphyrin-phospholipid peaks by uPLC-MS analysis.

Characterization of Size and Shape of Mn-Nanotexaphyrin:

Mn-nanotexaphyrin size was measured using a Malvern Nanosizer ZS90 (Malvern Instruments). Mn-nanotexaphyrin solutions were diluted in PBS and three measurements were performed with 15 runs each and the results averaged. Electron microscopy specimens were prepared by incubating 0.05 mg/mL Mn-nanotexaphyrin (5% PEG-lipid, 55% Mn-texaphyrin-phospholipid, and 40% cholesterol) on glow discharged carbon coated grids for 2 minutes, rinsing three times with milli-Q water and staining with 2% uranyl acetate. Samples were then visualized with a Tecnai F20 electron microscope (FEI Company) operating at 200 kV and images were recorded with a Tietz F114 CCD (TVIPS).

Serum Stability by T2-Evaluation:

Mn-nanotexaphyrin (0.35 mM) was incubated in 50% FBS at 37° C. (1 mL total volume), where T2 measurements were made at specified time intervals on a 1.5 T relaxometer (Minispec, Bruker® Corporation, Ettlingen, Germany).

In Vitro Relaxivity:

For in vitro measurements, the Biospec was equipped with a B-GA12 gradient coil insert and 7.2 cm inner diameter linearly-polarized cylindrical RF volume coil of Bruker manufacture. Following localization and tuning, coronal T1 and T2 maps with matching geometric features were acquired from samples within vertically-oriented Eppendorf tubes (400 pl), including 0.25 mm in-plane resolution, 180×128 matrix, 45×32 mm field-of-view, and 3 mm slice thickness. T1 mapping used a variable repetition time spin-echo technique (echo time 9.1 ms; 8 repetition times of 100, 250, 500, 750, 1000, 1500, 2500 and 4000 ms; scan time 8 min 29 sec). T2 mapping used a multi-echo spin-echo technique (48 echo times ranging from 10 to 480 ms; refocusing interval 10 ms; repetition time 6000 ms; scan time 9 min 36 sec).

In Vivo MRI:

All animals received human care in accordance with the policies formulated by the University Health Network (UHN) Animal Care Committee, the Animal for Research Act of the Province of Ontario, and the Canadian Council on Animal Care. All animal studies have been approved by the UHN Animal Care Committee protocols. Male New Zealand white rabbits (Charles River, Wilmington, Mass., USA) weighing from 2.0 to 3.5 kg were injected with 300 µL of VX-2 tumor cell suspension (5×106/mL) to induce tumor into the buccinator muscle. Tumors formed at the site of VX-2 cell injection and all rabbits presented with at least one cervical lymph node metastasis at two weeks post inoculation. One rabbit with lymph node metastasis confirmed by CT imaging was injected with 1.5 mL of 8 mg/mL of Mn-nanotexaphyrin subcutaneously surrounding the tumor area (similar to sentinel lymph node biopsy (SLNB) procedures using technetium-99). After 2 h injection, MRI was performed on a 7 Tesla preclinical MR imaging system (Biospec, Bruker® Corporation, Ettlingen, Germany) For rabbit images, imaging used the B-GA20S gradient coils and a 15.5 cm inner diameter quadrature cylindrical RF volume coil of Bruker manufacture. The rabbits were oriented in lateral decubitis position within a plexiglass holder, and inserted feet-first into the bore. Anaesthesia was delivered directly to a nose cone using a MR-compatible system. Coronal and axial T2-weighted imaging was performed at baseline, and coronal and axial T2-weighted and T1-weighted imaging was performed at 2 hours following subcutaneous contrast agent injection. All acquisitions shared a 1×1×1.5 mm spatial resolution. Coronal acquisitions shared a 110×80 mm field-of-view, 110×80 matrix size, and 36 slice coverage. Axial acquisitions shared a 96×72 mm field-of-view, 96×72 mm matrix size, and 55 slice coverage. All T2-weighted image sets were acquired with an effective echo time of 66.5 ms (echo time 9.5 ms; RARE factor of 14) and repetition time of 6000 ms. All T1-weighted image sets were acquired with an effective echo time of 9.5 ms (echo time 9.5 ms; RARE factor of 2) and repetition time of 1000 ms. Acquisition times ranged from 4 min 24 sec for coronal 72-weighted imaging, to 7 min 30 sec for axial r2-weighted imaging.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

[1] J. L. Sessler, G. Hemmi, T. D. Mody, T. Murai, A. Burrell, S. W. Young, *Accounts of Chemical Research* 1994, 27, 43-50.

[2] L. Sessler, T. D. Mody, G. W. Hemmi, V. Lynch, *Inorganic Chemistry* 1993, 32, 3175-3187.

[3] D. I. Rosenthal, P. Nurenberg, C. R. Becerra, E. P. Frenkel, D. P. Carbone, B. L. Lum, R. Miller, J. Engel, S. Young, D. Miles, *Clinical Cancer Research* 1999, 5, 739-745.

[4] R. A. Miller, K. Woodburn, Q. Fan, M. F. Renschler, J. L. Sessler, J. A. Koutcher, *International Journal of Radiation Oncology\*Biology\*Physics* 1999, 45, 981-989.

[5] J. L. Sessler, N. A. Tvermoes, D. M. Guldi, T. D. Mody, W. E. Allen, *The Journal of Physical Chemistry A* 1999, 103, 787-794.

[6] S. W. Young, F. Qing, A. Harriman, J. L. Sessler, W. C. Dow, T. D. Mody, G. W. Hemmi, Y. Hao, R. A. Miller, *Proceedings of the National Academy of Sciences* 1996, 93, 6610-6615.

[7] J. F. Arambula, J. L. Sessler, M. E. Fountain, W.-h. Wei, D. Magda, Z. H. Siddik, *Dalton Transactions* 2009, 48, 10834-10840.

[8] S. Young, M. Wright, J. Sessler, T. Mody, D. Magda, PCT Int Appl WO 1997, 46, 262.

[9] J. F. Lovell, C. S. Jin, E. Huynh, H. Jin, C. Kim, J. L. Rubinstein, W. C. Chan, W. Cao, L. V. Wang, G. Zheng, *Nature Materials* 2011, 10, 324-332.

[10] L. J. Boucher, *Journal of the American Chemical Society* 1968, 90, 6640-6645.

[11] a) H. L. M. Cheng, I. E. Haedicke, W. Cheng, J. Tchouala Nofiele, X. a. Zhang, *Journal of Magnetic Resonance Imaging* 2014, 40, 1474-1480; b) W. Cheng, I. E. Haedicke, J. Nofiele, F. Martinez, K. Beera, T. J. Scholl, H.-L. M. Cheng, X.-a. Zhang, *Journal of Medicinal Chemistry* 2014, 57, 516-520; c) Z. Zhang, R. He, K. Yan, Q.-n. Guo, Y.-g. Lu, X.-x. Wang, H. Lei, Z.-y. Li, *Bioorganic & Medicinal Chemistry Letters* 2009, 19, 6675-6678.

[12] A. E. Hansen, A. L. Petersen, J. R. Henriksen, B. Boerresen, P. Rasmussen, D. R. Elema, P. M. Rosenschoeld, A. T. Kristensen, A. Kjaer, T. L. Andresen, *ACS Nano* 2015, 9, 6985-6995.

[13] a) Y.-w. Jun, Y.-M. Huh, J.-s. Choi, J.-H. Lee, H.-T. Song, S. Kim, S. Kim, S. Yoon, K.-S. Kim, J.-S. Shin, *Journal of the American Chemical Society* 2005, 127, 5732-5733; b) R. A. Brooks, F. Moiny, P. Gillis, *Magnetic Resonance in Medicine* 2001, 45, 1014-1020.

[14] a) T. Sato, T. Iijima, M. Seki, N. Inagaki, *Journal of Magnetism and Magnetic Materials* 1987, 65, 252-256; b) H. Shokrollahi, *Materials Science and Engineering: C* 2013, 33, 4485-4497; c) D. Pan, A. H. Schmieder, S. A. Wickline, G. M. Lanza, *Tetrahedron* 2011, 67, 8431-8444.

The invention claimed is:

1. A method of preparing a texaphyrin-phospholipid conjugate, wherein the texaphyrin-phospholipid conjugate comprises a texaphyrin, texaphyrin derivative or texaphyrin analog covalently attached to a lipid side chain of a phospholipid, the texaphyrin derivative or texaphyrin analog having a core moiety represented by Formula I:

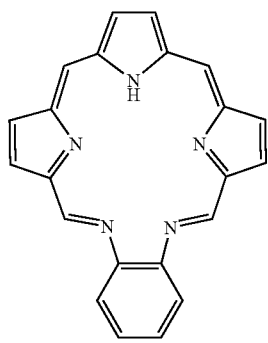

Formula I the method comprising reacting

6

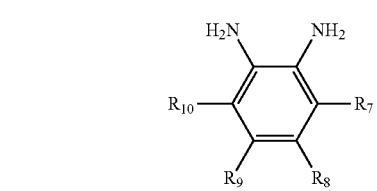

(6)

with

7

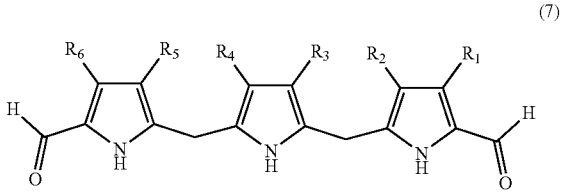

(7)

to yield

8

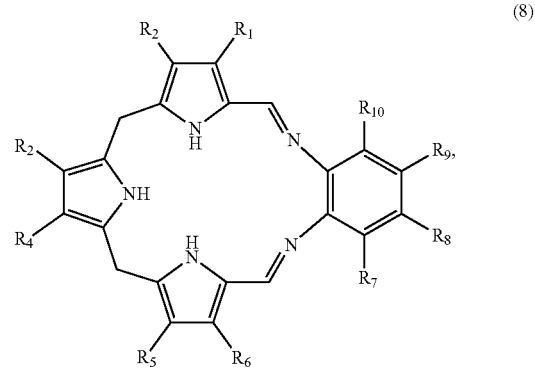

(8)

under hydrogen chloride and a temperature of between 50 to 52° C.;

where $R_1$-$R_6$ are each independently selected from the group consisting of H, an alkyl group, or an alkyl group substituted with an OH, SH, heteroalkyl, aryl, heteroaryl, or heterocyclic group;

one of $R_7$, $R_8$, $R_9$, and $R_{10}$ is a phospholipid moiety and the remainder of $R_7$-$R_{10}$ are each independently selected from H, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, and an acyl group;

wherein the phospholipid comprises phosphatidylcholine, phosphatidylethanoloamine, phosphatidylserine or phosphatidylinositol.

2. The method of claim 1, wherein is prepared by reducing:

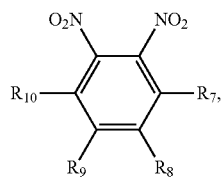
(5)

under hydrogen, Pd/C, and HCl;
wherein one of $R_7$, $R_8$, $R_9$, and $R_{10}$ is the phospholipid moiety, and the remainder of $R_7$-$R_{10}$ are each independently selected from H, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, and an acyl group.

3. The method of claim 2, wherein

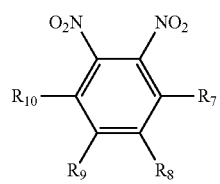
(5)

where one of $R_7$-$R_{10}$ is the phospholipid moiety and the remainder of $R_7$-$R_{10}$ are each independently selected from H, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, and an acyl group is prepared by reacting a) 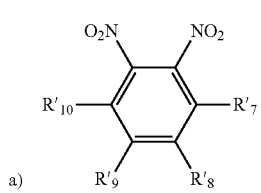
(4)

where one of $R'_7$-$R'_{10}$ is a carbon chain linker represented by Formula A

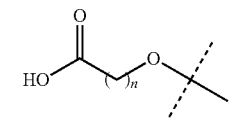
Formula A with n=1 to 20, and the remainder of $R'_7$-$R'_{10}$ are each independently selected from H, an alkyl group, a heteroalkyl group, a cycloalkyl group, an alkenyl group, a heteroalkenyl group, an alkynyl group, a heteroalkynyl group, an aryl group, a heteroaryl group, a heterocyclic group, and an acyl group;

with b) the phospholipid in the presence of EDC, DIPEA, and DMAP.

4. The method of claim 1, further comprising synthesizing the texaphyrin, texaphyrin derivative or texaphyrin analog, comprising cleaving the texaphyrin, texaphyrin derivative or texaphyrin analog from the conjugate.

5. The method of claim 4, wherein the cleaving is performed using an enzyme.

6. The method of claim 1, wherein the phospholipid is branched or unsaturated.

7. The method of claim 1, wherein the phospholipid moiety is

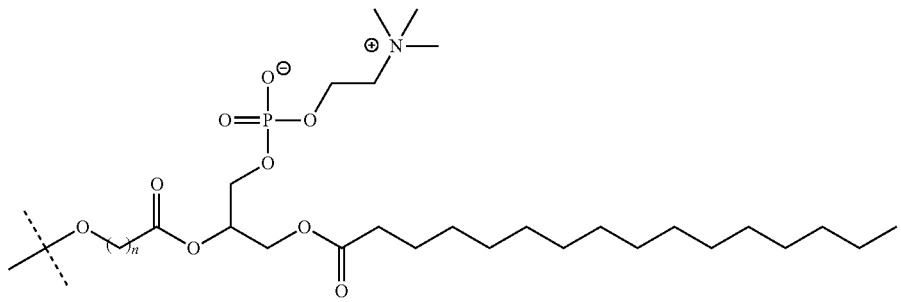

where n is 0 to 20.

8. The method of claim 3, wherein:

compound (4) is

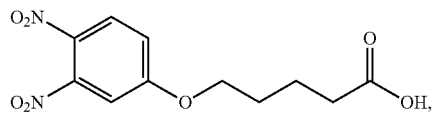
4 the phospholipid is
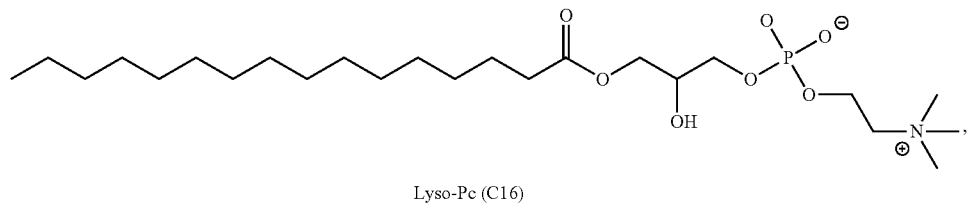
Lyso-Pc (C16)
compound (5) is
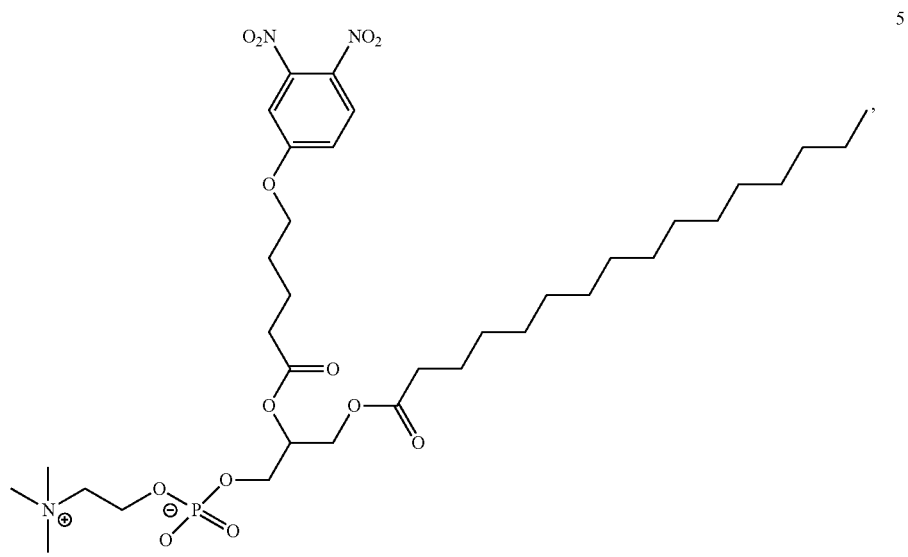
compound (6) is
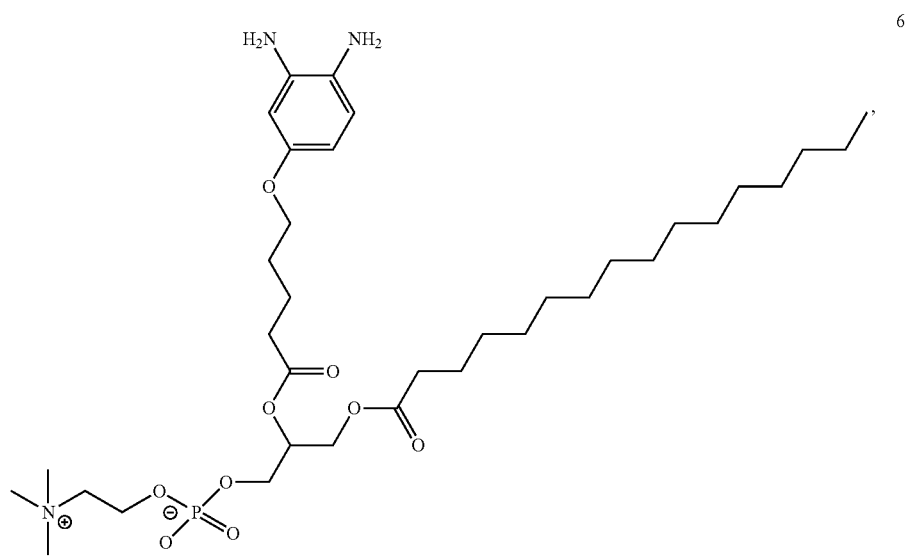

compound (7) is

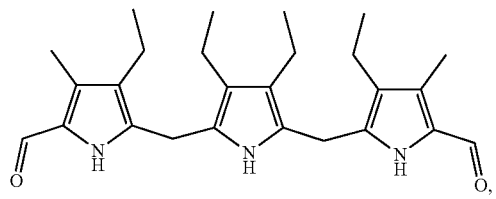

and
compound (8) is selected from Mn, Fe, Co, Zn, Y, Cd, In, La, Hg, Pb, Bi, Ce, Pr, Nd, Sm, Eu, Gd, Tb, Dy, Ho, Er, Tm, Yb, and Lu.

14. The method of claim 1, further comprising forming a nanoparticle comprising the texaphyrin-phospholipid conjugate defined in claim 1, wherein the nanoparticle comprises at least 15, 25, 35, 45, 55, 65, 75, 85, 95 or 100 molar % texaphyrin-phospholipid conjugate.

15. The method of claim 14, wherein the nanoparticle further comprises a pegylated material selected from PEG, PEG-lipid, and PEG-DSPE.

16. The method of claim 15, wherein the pegylated material is present in an amount of about 5 molar %.

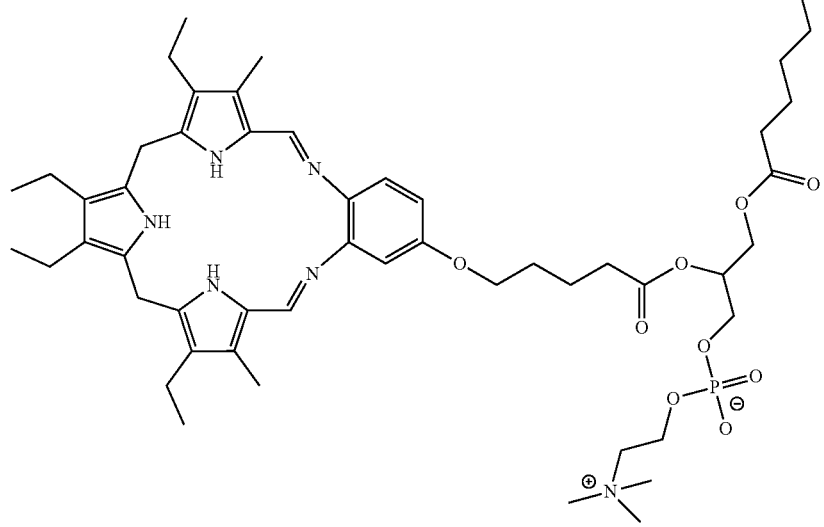

9. The method of claim 1, wherein the texaphyrin, texaphyrin derivative or texaphyrin analog is attached to the lipid side chain at the sn-1 or the sn-2 position.

10. The method of claim 1, wherein the texaphyrin, texaphyrin derivative or texaphyrin analog is texaphyrin.

11. The method of claim 1, wherein the phospholipid comprises an acyl side chain of 12 to 22 carbons.

12. The method of claim 1, wherein the texaphyrin, texaphyrin derivative or texaphyrin analog is conjugated to the glycerol group on the phospholipid by a carbon chain linker of 0 to 20 carbons.

13. The method of claim 1, further comprising complexing the texaphyrin-phospholipid conjugate with a metal 17. The method of claim 14, wherein the nanoparticle is a bilayered vesicle or a monolayered vesicle.

18. The method of claim 14, wherein the nanoparticle is substantially spherical and between about 3 nm and about 200 nm in diameter.

19. The method of claim 14, further comprising encapsulating an active agent therein.

20. The method of claim 14, wherein the nanoparticle further comprises a targeting molecule.

* * * * *